US008670820B2

(12) United States Patent
Gutfinger et al.

(10) Patent No.: US 8,670,820 B2
(45) Date of Patent: Mar. 11, 2014

(54) NEAR FIELD-BASED SYSTEMS AND METHODS FOR ASSESSING IMPEDANCE AND ADMITTANCE FOR USE WITH AN IMPLANTABLE MEDICAL DEVICE

(75) Inventors: Dan E. Gutfinger, Agoura Hills, CA (US); Fujian Qu, Sunnyvale, CA (US); Alex Soriano, Ventura, CA (US); Ryan Rooke, Redondo Beach, CA (US); Yelena Nabutovsky, Sunnyvale, CA (US); Riddhi Shah, Mountain View, CA (US); Andreas Blomqvist, Taby (SE)

(73) Assignee: Pacesetter, Inc., Sylmar, CA (US)

( * ) Notice: Subject to any disclaimer, the term of this patent is extended or adjusted under 35 U.S.C. 154(b) by 791 days.

(21) Appl. No.: 12/853,130

(22) Filed: Aug. 9, 2010

(65) Prior Publication Data
US 2012/0035493 A1   Feb. 9, 2012

(51) Int. Cl.
*A61B 5/053* (2006.01)

(52) U.S. Cl.
USPC ........... 600/513; 600/508; 600/509; 600/512; 607/24; 607/28

(58) Field of Classification Search
USPC .............. 600/508, 509, 512, 513; 607/24, 28
See application file for complete search history.

(56) References Cited

U.S. PATENT DOCUMENTS

| | | | |
|---|---|---|---|
| 4,674,518 A | 6/1987 | Salo | |
| 6,249,705 B1 | 6/2001 | Snell | |
| 6,328,699 B1 | 12/2001 | Eigler et al. | |
| 6,438,408 B1 | 8/2002 | Mulligan et al. | |
| 6,480,733 B1 | 11/2002 | Turcott | |
| 6,512,949 B1 | 1/2003 | Combs et al. | |
| 6,512,952 B2 | 1/2003 | Stahmann et al. | |
| 6,572,557 B2 | 6/2003 | Tchou et al. | |
| 6,628,988 B2 | 9/2003 | Kramer et al. | |
| 6,643,546 B2 | 11/2003 | Mathis et al. | |
| 6,643,548 B1 | 11/2003 | Mai et al. | |
| 6,645,153 B2 | 11/2003 | Kroll et al. | |
| 6,741,885 B1 | 5/2004 | Park et al. | |
| 6,748,261 B1 | 6/2004 | Kroll et al. | |
| 6,829,503 B2 | 12/2004 | Alt | |
| 6,970,742 B2 | 11/2005 | Mann et al. | |
| 7,115,095 B2 | 10/2006 | Eigler et al. | |

(Continued)

OTHER PUBLICATIONS

Bini, G.C. et al. "A Method to Calculate Tissue Impedance through a Standard Bipolar Pacing Lead," Cardiovasc Eng. 2006;6:45-52.

(Continued)

*Primary Examiner* — Carl H Layno
*Assistant Examiner* — Eugene Wu

(57) ABSTRACT

A new model is provided for understanding and exploiting impedance or admittance values measured by implantable medical devices, such as pacemakers or cardiac resynchronization devices (CRTs.) The device measures impedance along vectors extending through tissues of the patient between various pairs of electrodes. The device then converts the vector-based impedance measurements into near-field individual electrode-based impedance values. This is accomplished, in at least some examples, by converting the vector-based impedance measurements into a set of linear equations to be solved while ignoring far-field contributions to the impedance measurements. The device solves the linear equations to determine the near-field impedance values for the individual electrodes, which are representative of the impedance of tissues in the vicinity of the electrodes. The device then performs or controls various device functions based on the near-field values, such as analyzing selected near-field values to detect heart failure or pulmonary edema.

29 Claims, 24 Drawing Sheets

(56) References Cited

U.S. PATENT DOCUMENTS

| | | | |
|---|---|---|---|
| 7,139,609 | B1 | 11/2006 | Min et al. |
| 7,272,443 | B2 | 9/2007 | Min et al. |
| 7,437,192 | B2 | 10/2008 | Gill et al. |
| 7,483,743 | B2 | 1/2009 | Mann et al. |
| 7,502,644 | B2 | 3/2009 | Gill et al. |
| 7,505,814 | B2 | 3/2009 | Bornzin et al. |
| 2008/0262361 | A1 | 10/2008 | Gutfinger et al. |
| 2009/0018597 | A1 | 1/2009 | Wenzel et al. |
| 2010/0023069 | A1* | 1/2010 | Moffitt et al. .............. 607/2 |
| 2011/0009927 | A1* | 1/2011 | Parker et al. .............. 607/62 |
| 2012/0165692 | A1* | 6/2012 | Hollmark et al. .............. 600/518 |

OTHER PUBLICATIONS

Braunwald, Eugene MD, "Mitral Regurgitation: Physiological, Clinical and Surgical Considerations," from Seminars in Medicine of the Beth Israel Hospital, Boston, reprinted from N Engl J Med. Aug. 21, 1969; 281:425-433.

Burch, G.E. MD et al, "The syndrome of papillary muscle dysfunction," Am Heart J. 1968;75:399-415.

Cheng, Tsung O. MD, "Some New Observations on the Syndrome of Papillary Muscle Dysfunction," Am J Med. 1969;47:924-945.

De Busk, robert F. MD et al., "The clinical spectrum of papillary muscle disease," in Medical Progress reprinted from N Engl J Med. 1969;281:1458-1467.

Khoury, Dirar S. PhD et al., "Ambulatory Monitoring of Congestive Heart Failure by Multiple Bioelectric Impedance Vectors," J Am Coll Cardiol, 2009; 53(12):1075-1081.

Levine, Robert A. MD et al., "Ischemic Mitral Regurgitation on the Threshold of a Solution From Paradoxes to Unifying Concepts," Circulation. 2005;112:745-758.

Ritzema, Jay MRCP et al. "Physician-Directed Patient Self-Management of Left Atrial Pressure in Advanced Chronic Heart Failure," Circulation. 2010;121:1086-1095.

Schlant, Robert C. MD, "The Management of Chronic Mitral Regurgitation," Council on Clinical Cardiology Newletter, editted by Beller. 1986;12(1)::1-9.

* cited by examiner

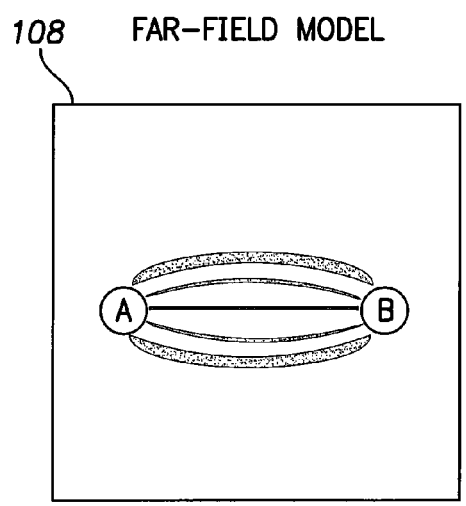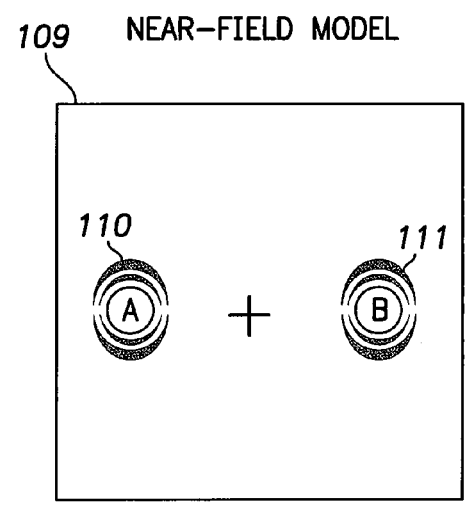
FIG. 3A
PRIOR ART
FIG. 3B

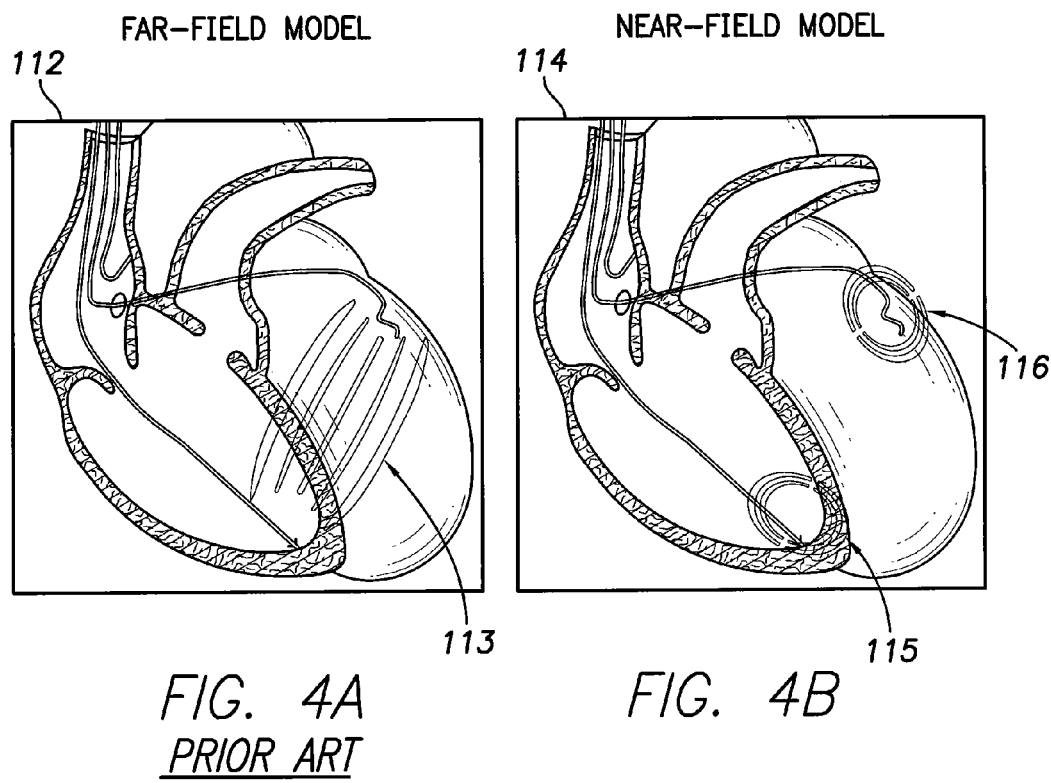

IMPEDANCE TRIANGLE
THREE ELECTRODE EXAMPLE
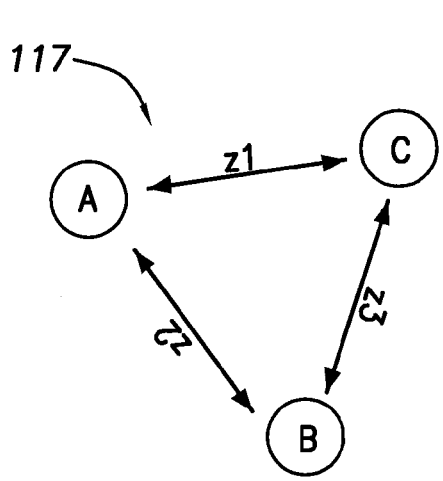
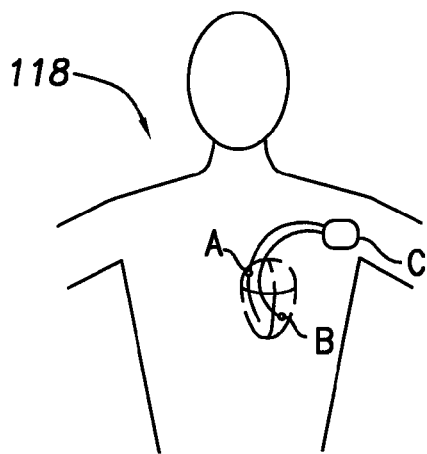
$z1 = A + C$
$z2 = A + B$
$z3 = B + C$
$z1 + z2 - z3 = 2A$
$z2 + z3 - z1 = 2B$
$z1 + z3 - z2 = 3C$
FIG. 5

ANALYTIC SOLUTION

```
v1 = LVr+Case
v2 = RVr+Case
v3 = RAr+Case
v4 = RVc+Case
v5 = LVr+RAr
v6 = LVr+RVr
```
— 216

```
e1 = [(v1−v2) + v6 + (v1−v3) + v5]/4 =
     [(LVr−RVr) + (LVr+RVr) + (LVr−RAr) + (LVr+RAr)]/4 = LVr
e2 = [(v2−v1) + v6]/2 = [(RVr−LVr) + (LVr+RVr)]/2 = RVr
e3 = [(v3−v1) + v5]/2 = [(RAr−LVr) + (LVr+RAr)]/2 = RAr
e4 = [(v1−e1) + (v2−e2) + (v3−e3)]/3 = Case
e5 = v4 − e4 = Coil
```
— 218

SOLUTION IN MATRIX FORM

— 219

$$\begin{pmatrix} LVr \\ RVr \\ RAr \\ Case \\ Coil \end{pmatrix} = \begin{bmatrix} 0.5 & -0.25 & -0.25 & 0 & 0.25 & 0.25 \\ -0.5 & 0.5 & 0 & 0 & 0 & 0.5 \\ -0.5 & 0 & 0.5 & 0 & 0.5 & 0 \\ 0.5 & 0.25 & 0.25 & 0 & -0.25 & -0.25 \\ -0.5 & -0.25 & -0.25 & 1 & 0.25 & 0.25 \end{bmatrix} \times \begin{pmatrix} V1 \\ V2 \\ V3 \\ V4 \\ V5 \\ V6 \end{pmatrix}$$

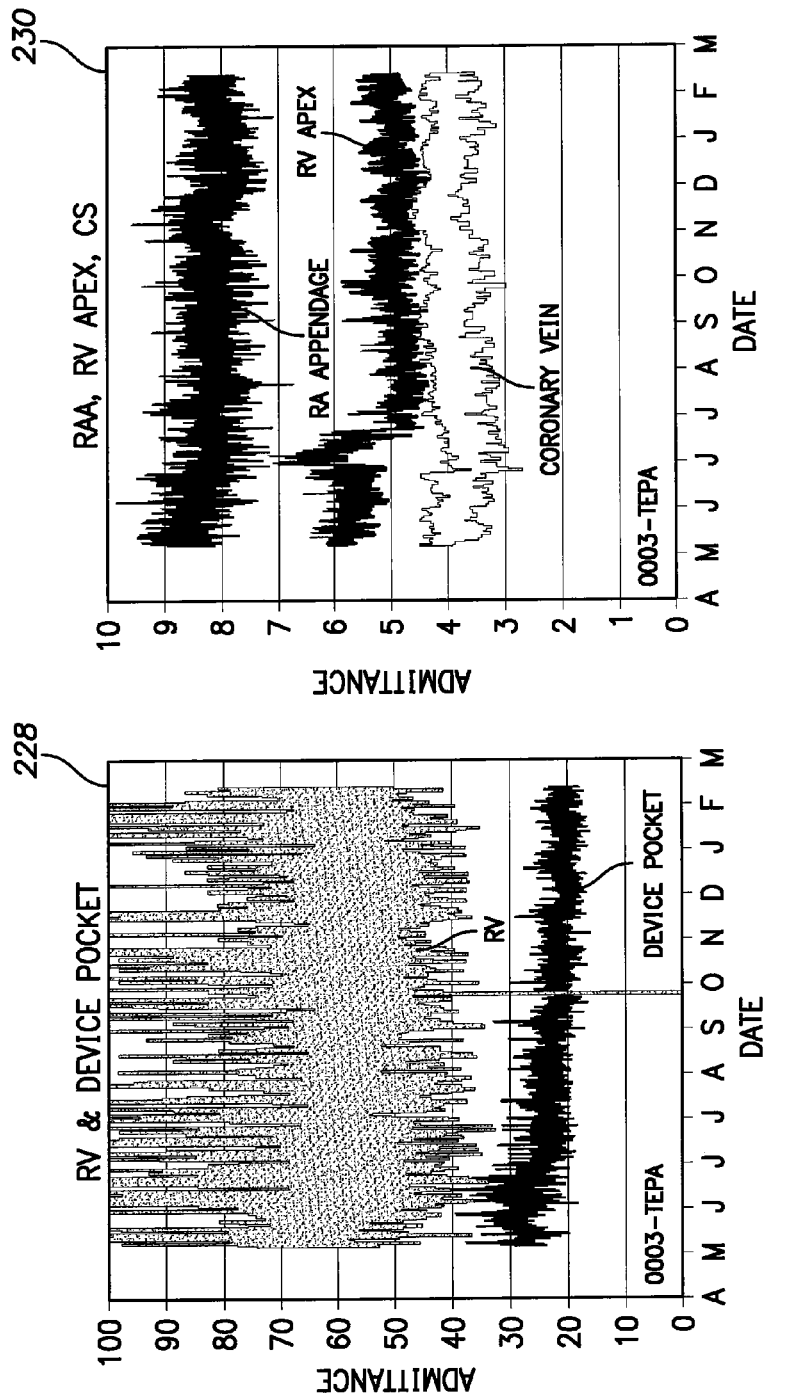

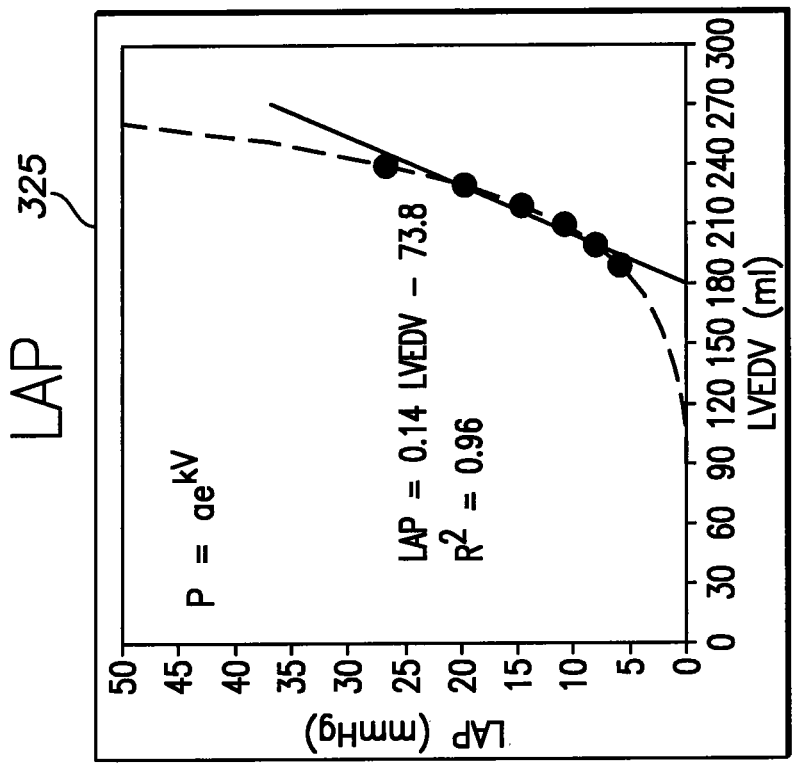
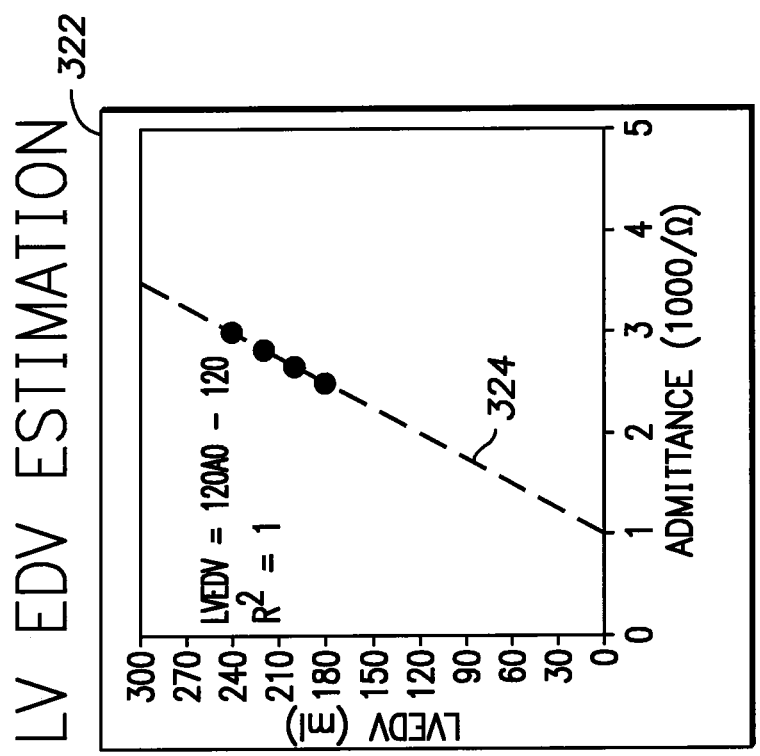
FIG. 16

NEAR FIELD-BASED SYSTEMS AND METHODS FOR ASSESSING IMPEDANCE AND ADMITTANCE FOR USE WITH AN IMPLANTABLE MEDICAL DEVICE

CROSS REFERENCE TO RELATED APPLICATIONS

This application is related to U.S. patent application Ser. No. 12/853,157, filed concurrently herewith, titled "Systems and Methods for Estimating Left Atrial Pressure (LAP) in Patients with Acute Mitral Valve Regurgitation for Use by an Implantable Medical Device".

FIELD OF THE INVENTION

The invention relates to implantable medical devices such as pacemakers, implantable cardioverter defibrillators (ICDs) and cardiac resynchronization therapy (CRT) devices and in particular to techniques for assessing impedance and/or admittance values measured by such devices.

BACKGROUND OF THE INVENTION

State-of-the-art implantable medical devices are often equipped to measure impedance (or related electrical parameters such as admittance) between various pairs of electrodes implanted within the patient. Examples include intracardiac impedance measurements made between pairs of electrodes mounted to leads implanted on or within the various chambers of the heart. Other examples include intrathoracic impedance measurements made between the housing of the device (or "can" electrode) and electrodes implanted on or within the heart. Traditionally, such impedance measurements were deemed to be representative of the electrical impedance along a vector between the electrodes. That is, impedance measurements were associated with a particular pair of electrodes or some combination of three or more electrodes. Herein, these measurements are generally referred to as "vector-based" impedance measurements because the measurements are associated with at least one pair of electrodes and the vectors therebetween. In terms of analyzing and interpreting the measured impedance data, the interpretation typically relied on a conceptual model wherein the measured impedance was deemed to be representative of the impedance of the field between the electrodes pairs, including far-field contributions to that impedance. This model is referred to herein as the "far-field model" of impedance. Under the far-field model, impedance measured along a vector between a pair of electrodes A and B is deemed to be representative of the field between A and B.

As one example of the far-field model, intrathoracic impedance measurements made between the device housing and a cardiac electrode implanted within the heart are deemed to represent the impedance to electrical flow spanning a field extending through the lungs between the device and the cardiac electrode. This intrathoracic vector-based impedance measurement is then used to, for example, assess pulmonary fluid congestion to detect pulmonary edema (PE) or heart failure (HF.) Although this traditional interpretation of the impedance measurements can be useful, the present inventors have recognized that an alternative interpretation of impedance measurements based on a "near-field model" can provide a more useful means for understanding, analyzing and interpreting impedance measurements.

The present invention is generally directed to the new near-field impedance model and to various systems, methods and applications that exploit the new model.

SUMMARY OF THE INVENTION

In accordance with an exemplary embodiment of the invention, a method is provided for use with an implantable medical device—such as a pacemaker, ICD or CRT device—for determining and exploiting near-field immittance values (wherein "immittance" broadly refers to impedance, conductance, admittance or other generally equivalent electrical values or parameters) associated with individual electrodes in accordance with a near-field model that associates immittance values with individual electrodes rather than with pairs of electrodes or with the vectors therebetween. In one example, the device detects vector-based immittance measurements within tissues of the patient using a plurality of electrodes coupled to the device. The device then converts the vector-based immittance measurements into relative near-field individual electrode-based immittance values, which are then exploited to control various device functions, such as to control the delivery of therapy in response to medical conditions detected using the near-field immittance values or to control the storage of diagnostic data. It should be understood that any function that the device can perform or control, alone or in combination with other devices, is a "device function." This includes, but is not limited to, detecting medical conditions such a PE or HF, detecting cardiac parameters such as left atrial pressure (LAP) or left ventricular end diastolic volume (LV EDV), controlling pacing, and generating and transmitting diagnostic information, etc.

In this regard, exemplary techniques provided herein exploit the aforementioned near-field model, which offers a new perspective for the interpretation of the impedance (or admittance) measurements that significantly simplifies the analysis and interpretation of data and the development of detection methods/procedures. Briefly, the near-field model is based on the recognition that the impedance along a vector between a pair of electrodes (A and B) can be modeled as a superposition of near-field impedance values that are associated with the individual electrodes (i.e. A+B). That is:

Traditional Model: Impedance=A to B=Field between A and B

New Model Impedance=A+B=Near-Field A+Near-Field B

More generally, the near-field model transforms multiple vector-based or pair-based immittance measurements into a set of individual electrode-based near-field immittance values that can be interpreted and analyzed more easily by the device. In an example with N electrodes where impedance is measured (where N is at least three), the conversion of vector-based impedance measurements into near-field impedance values is performed by converting N vector-based impedance measurements ($v1, v2, \ldots, vN$) into a set of linear equations to be solved by ignoring far-field contributions to impedance. The set of linear equations are then solved to yield a set of relative near-field impedance values ($e1, e2, \ldots, eN$) associated with the individual electrodes. In other examples, N+1 vectors (or some even larger number of vectors) are used to determine the near-field impedances of the N electrodes.

One important advantage of the near-field model is that by deriving near-field impedance associated with individual electrodes, the device can easily associate a specific physical entity—such as the particular anatomical structure adjacent to the electrode—with the corresponding near-field impedance value. For example, for a left ventricular ring electrode (LVring or LVr), the corresponding near-field impedance is associated with the local fluid and tissue content surrounding the LVring electrode within the coronary vein and adjacent left ventricular myocardium and pericardial space. For a right ventricular ring electrode (RVring or RVr), the corresponding near-field impedance is associated with the local fluid and tissue content within the adjacent RV cavity and RV myocardium (e.g., RV apex). For the RAring (or "RAr" electrode), the corresponding near-field impedance is associated with the local fluid and tissue content within the adjacent RA cavity and RA tissues (e.g., RA appendage). For the device case or housing, the corresponding near-field impedance is associated with the local fluid and tissue content surrounding the device case within the subcutaneous pocket and adjacent tissues. For the RVcoil, the corresponding near-field impedance is associated with the local fluid and tissue content surrounding the RVcoil electrode within the RV chamber.

Moreover, by determining near-field impedance or admittance (immittance) values corresponding to particular electrodes, a variety of useful applications are available to the device such as: detecting lead anomalies; detecting lead infections, cardiac perforations, or lead abrasions; detecting device pocket infections; confirming the initiation or termination of pacing; estimating LV and RV volume parameters such as LV EDV and RV end diastolic volume (RV EDV); estimating LAP; and detecting HF or PE events.

Note that the examples described herein are directed to bipolar impedance rather than quadripolar impedance. In order to measure impedance, the device sends out a current between a pair of electrode (herein "current electrodes") and records voltage from a pair of electrodes (herein "voltage electrodes.") The voltage electrodes may or may not be the same as the current electrodes. In the case where the voltage electrodes are the same as the current electrodes, the impedance collected is called "bipolar impedance." If not the same, then the impedance is called "tripolar or quadripolar impedance" depending on whether one pair of voltage and current electrodes is different ("tripolar") versus two pairs of voltage and current electrodes are different ("quadrapolar"). Although some aspects of the invention are generally and broadly applicable to either bipolar impedance or quadripolar impedance, the interpretation of the resulting "individual electrode-based" impedance values may be unclear, particularly if the current and voltage nodes are not in close proximity to one another. Hence, the invention is primarily intended to be practiced for use with bipolar impedance or for use in quadripolar cases where the current and voltage nodes are in close proximity to one another.

A wide variety of other applications and methods are performed in accordance with the general invention. These are just some examples.

BRIEF DESCRIPTION OF THE DRAWINGS

Further features and advantages of the invention may be more readily understood by reference to the following description taken in conjunction with the accompanying drawings, in which:

FIGS. 3A and 3B are a graphical illustrations comparing the far-field and near-field models of impedance, the latter of which is exploited by the method of FIG. 2;

FIGS. 4A and 4B provide simplified, partly cutaway views, of the heart of a patient along with various leads, and which particularly illustrates a comparison of far-field and near-field impedance zones, the latter of which is exploited by the method of FIG. 2;

FIG. 5 is a graphical illustration of an impedance triangle corresponding to a simplified three electrode example of the near-field impedance technique exploited by the method of FIG. 2;

FIG. 8 is a diagram illustrating aspects of the procedure of FIG. 7, and particularly illustrating the calculation of near-field impedance values for a six vector and a five electrode example, both in analytic and matrix form;

FIG. 16 provides exemplary graphs corresponding to data that can be processed by the procedure of FIG. 11 to detect LV volume, which particularly illustrate a correlation between near-field admittance and LV EDV;

DESCRIPTION OF THE PREFERRED EMBODIMENTS

The following description includes the best mode presently contemplated for practicing the invention. The description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Overview of Implantable Medical System

Figure 1:
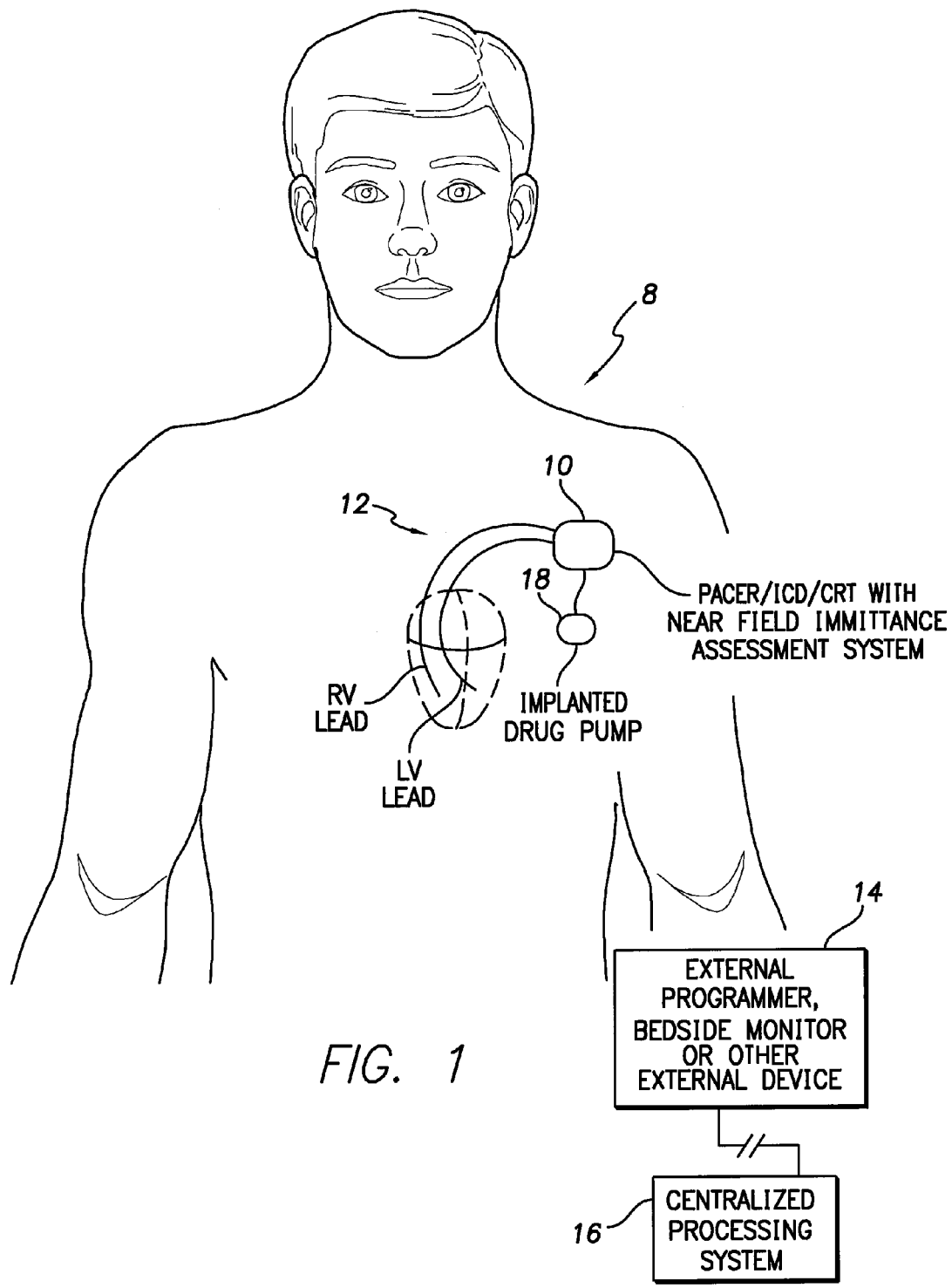
FIG. 1 is a stylized representation of an exemplary implantable medical system equipped with a system for assessing and exploiting near-field immittance values (i.e. impedance and/or admittance values)

FIG. 1 provides a stylized representation of an exemplary implantable pacing medical system 8 capable of assessing the near-field immittance of individual electrodes, i.e. the impedance, admittance or equivalent electrical parameters associated with a near-field zone surrounding a given electrode. The system is further capable of estimating various cardiac parameters, such as heart chamber volumes or pressure parameters, based on the near-field immittance values. The pacer/ICD may also be equipped to detect and track HF and/or PE based on the near-field impedance or admittance values. That is, the device is equipped to exploit the aforementioned near-field model to perform various useful detection or estimation functions.

Figure 20:
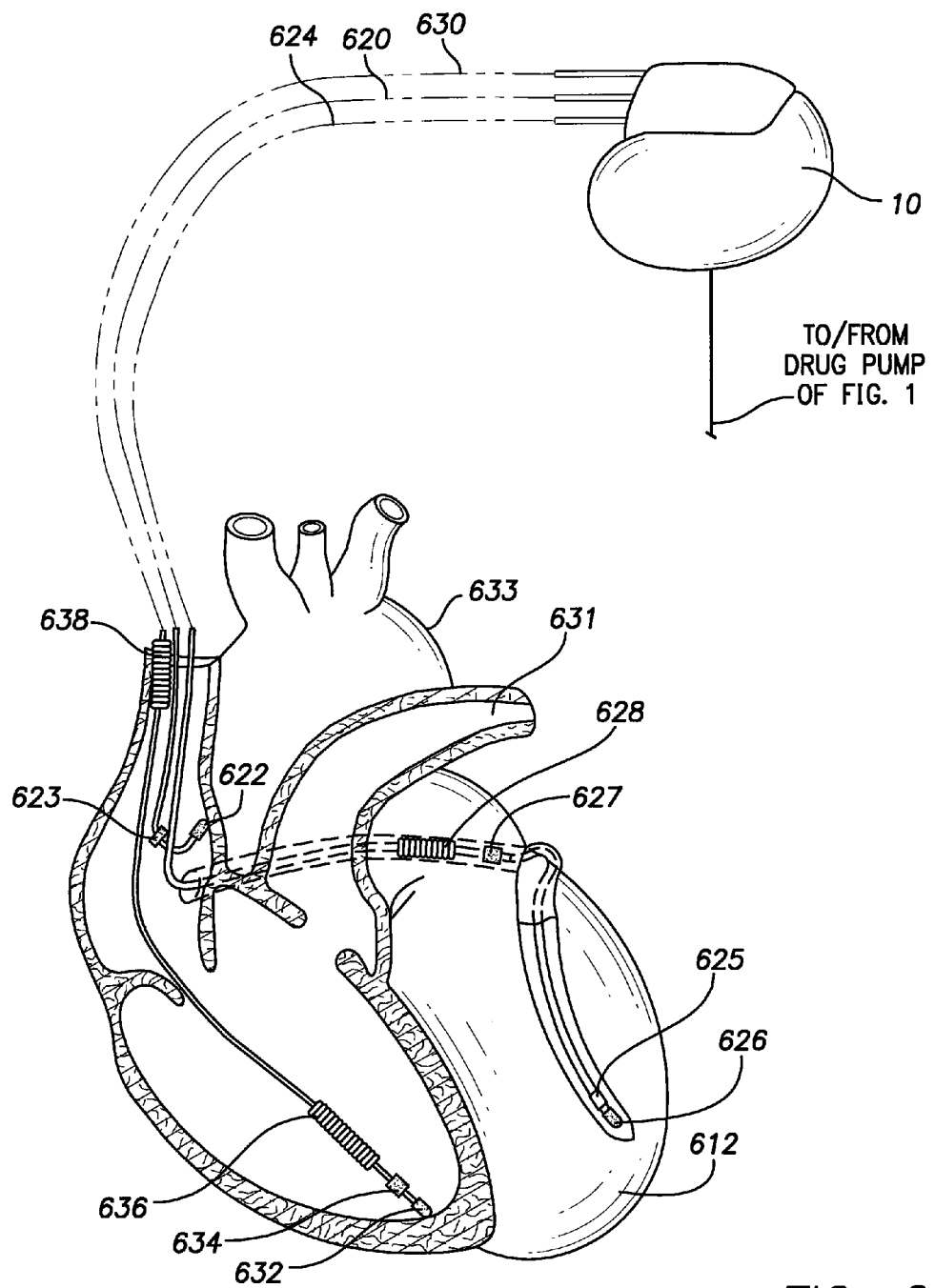
FIG. 20 is a simplified, partly cutaway view, illustrating the pacer/ICD of FIG. 1 along with a set of leads implanted in the heart of the patient.

To these and other ends, implantable medical system 8 includes a pacer/ICD/CRT device 10 or other cardiac stimulation device equipped to detect vector-based impedance measurements along vectors between various pairs of electrodes within a set of leads 12. In the examples described herein, the measurements are impedance measurements but other related parameters might be detected such as admittance. The device is further equipped to convert the vector-based impedance values into relative near-field impedance values corresponding to individual electrodes. Various cardiac parameters are then determined by the device based on the near-field impedance values, such as LAP or LV EDV. For brevity herein, implantable device 10 will be referred to as a pacer/ICD but it should be understood that other devices such as standalone CRT devices may instead be employed. Note also that in FIG. 1, only two leads are shown. A more complete representation of a set of leads is illustrated in FIG. 20, which is discussed below.

Depending upon the conditions or parameters detected, the pacer/ICD can issue warning signals, if appropriate. For example, if LAP is found to exceed a threshold indicative of HF or is rapidly increasing toward the threshold, warning signals may be generated to warn the patient, either using an internal warning device (which can be part of the pacer/ICD) or using an external bedside monitor/handheld warning device 14. The internal warning device may be a vibrating device or a "tickle" voltage device that, in either case, provides perceptible stimulation to the patient to alert the patient so that the patient may consult a physician. In one example, once the warning is felt, the patient positions an external warning device above his or her chest. The handheld device, which might be a personal advisory module (PAM), receives short-range telemetry signals from the implanted device and provides audible or visual verification of the warning signal. The handheld warning device thereby provides confirmation of the warning to the patient, who might otherwise be uncertain as to the reason for the internally generated warning signal. For further information regarding this warning/notification technique, see U.S. patent application Ser. No. 11/043, 612, of Kil et al., filed Jan. 25, 2005.

If a bedside monitor is provided, the bedside monitor provides audible or visual alarm signals to alert the patient or caregivers, as well as providing textual or graphic displays. In addition, any diagnostic information pertaining to a deteriorating cardiac condition of the patient is transferred to the bedside monitor or is stored within the pacer/ICD for subsequent transmission to an external programmer (not shown in FIG. 1) for review by a physician or other medical professional. The physician may then prescribe therapies to address the condition. The physician may also adjust the operation of the pacer/ICD to activate, deactivate or otherwise control any therapies that are automatically applied. The bedside monitor may be directly networked with an internet network site or a centralized computing system 16 for immediately notifying the physician of any urgent medical condition. The centralized system may include such systems as Merlin.Net of St. Jude Medical, which may be used in conjunction with bedside monitors or similar devices such as the HouseCall™ remote monitoring system or the Merlin@home systems, also of St. Jude Medical.

In response to an increasing and excessive LAP level or in response to the detection of HF or PE, the device can initiate various pacing therapies. One such therapy is CRT, which seeks to normalize asynchronous cardiac electrical activation and the resultant asynchronous contractions by delivering synchronized pacing stimulus to the ventricles. The pacing stimulus is typically synchronized so as to help to improve overall cardiac function. This may have the additional beneficial effect of reducing the susceptibility to life-threatening tachyarrhythmias. CRT and related therapies are discussed in, for example, U.S. Pat. No. 6,643,546 to Mathis et al., entitled "Multi-Electrode Apparatus And Method For Treatment Of Congestive Heart Failure"; U.S. Pat. No. 6,628,988 to Kramer et al., entitled "Apparatus And Method For Reversal Of Myocardial Remodeling With Electrical Stimulation"; and U.S. Pat. No. 6,512,952 to Stahmann et al., entitled "Method And Apparatus For Maintaining Synchronized Pacing."

In addition to CRT, other forms of therapy may also be controlled by the pacer/ICD in response to the detection of HF and PE or in response to changes in LAP or other cardiac parameters detected using the near-field impedance or admittance values. In this regard, if the implanted system is equipped with a drug pump or drug infusion device 18, appropriate medications may be automatically administered upon detection of a significant increase in LAP due to heart failure or cardiogenic PE. For example, medications may be delivered directly to the patient via the drug pump, if warranted. Alternatively, if a drug pump is not available, the patient may be provided with instructions—generated depending on LAP estimates or other parameters—specifying the dosage of various heart failure medications to be taken. Exemplary heart failure medications include angiotensin-converting enzyme (ACE) inhibitors such as captopril, enalapril, lisinopril and quinapril, diuretics, digitalis, nitrates, beta-blockers, inotropes, and other compounds. Depending upon the particular medication, alternative compounds (e.g., intravenous or subcutaneous agents) may be required for use in connection with an implantable drug pump. Routine experimentation may be employed to identify medications for treatment of heart failure or other conditions that are safe and effective for use in connection with an implantable drug pump. Dosages may be titrated based upon the severity of HF as determined from LAP or other parameters.

Figure 2:
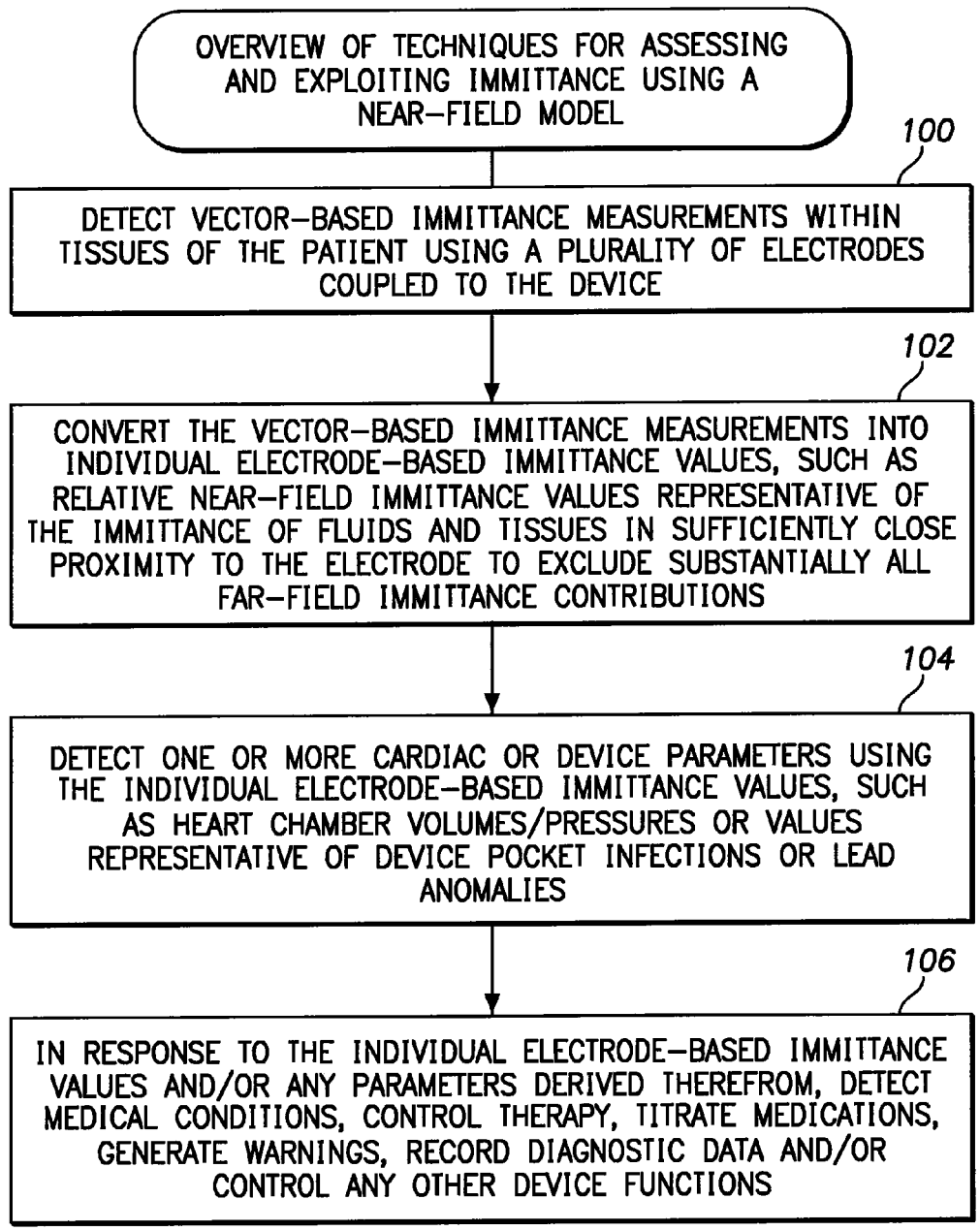
FIG. 2 provides an overview of techniques for assessing and exploiting near-field immittance values that may be performed by the system of FIG. 1.

FIG. 2 broadly summarizes the near-field assessment and exploitation techniques performed by the pacer/ICD of FIG. 1 or other suitably-equipped implantable devices. That is, the figure illustrates a general method that exploits the aforementioned near-field model. At step 100, the device detects vector-based immittance measurements (i.e. impedance and/or admittance values) within tissues of the patient using a plurality of electrode pairs coupled to the device. At step 102, the device converts the vector-based immittance measurements into individual electrode-based immittance values, such as relative near-field immittance values representative of the immittance of fluids and tissues in sufficiently close proximity to the electrode to exclude substantially all far-field immittance contributions.

At step 104, the device detects one or more cardiac parameters or device operation parameters using the individual electrode-based immittance values, such as heart chamber volumes/pressures or values representative of device pocket infections or lead anomalies. At step 106, in response to the individual electrode-based immittance values and/or the various parameters derived therefrom, the device selectively controls therapy, titrates medications, generates warnings, records diagnostic data or controls any other device function. As noted above, it should be understood that any function that the device can perform or control, alone or in combination with other devices, is a "device function." This includes, but is not limited to, detecting medical conditions such a PE or HF, detecting cardiac parameters such as LAP or LV EDV, detecting pacing/defibrillation lead anomalies, detecting infection, controlling pacing, and generating and transmitting diagnostic information, etc.

Hence, FIGS. 1 and 2 provide an overview of an implantable medical system/method for assessing and exploiting impedance and/or admittance values using the near-field model and for controlling numerous device functions in response thereto. Embodiments may be implemented that do not necessarily perform all of the functions described herein. For example, embodiments may be implemented that determine near-field immittance and detect medical conditions in response to changes in near-field immittance but do not automatically initiate or adjust therapies. Moreover, systems provided in accordance with the invention need not include all of the components shown in FIG. 1. In many cases, for example, the system will include only a pacer/ICD and its leads. Implantable drug pumps are not necessarily implanted. These are just a few exemplary embodiments. No attempt is made herein to describe all possible combinations of components that may be provided in accordance with the general principles of the invention. In addition, note that the particular locations of the implanted components shown in FIG. 1 are merely illustrative and may not necessarily correspond to actual implant locations. Although internal signal transmission lines provided are illustrated in FIG. 1 for interconnecting various implanted components, wireless signal transmission may alternatively be employed, where appropriate.

In the following section, additional explanatory information regarding the near-field model is provided so as to expand upon and clarify the brief descriptions of the near-field model discussed above.

The Near-field Model

The traditional far-field model of impedance characterizes vector-based impedance measurements as representing the impedance to electrical flow between a pair of electrodes, including far-field contributions to that impedance. With the near-field model, a new perspective is provided and exploited wherein the impedance measurements made using a pair of electrodes is deemed to represent the impedance contributions from local fluids and tissues near the electrodes under the assumption that any contribution to the measurement from the far-field of the inter-electrode space can be ignored. For example, for the LVring to case vector, the near-field corresponds to tissues surrounding the LVring electrode within the coronary vein and the adjacent left ventricular myocardium/cavity and pericardial space, along with the local tissues surrounding the device case within the subcutaneous pocket.

That is, with the near-field model, the measured impedance along a vector comprising two electrodes (A and B) is simplified to reflect a superposition (i.e. summation) of the near-field impedance measurements associated with each of the individual electrodes, while assuming that any contribution from the far-field inter-electrode space can be ignored. This is generally illustrated in FIGS. 3A and 3B for an example wherein a bipolar intrathoracic impedance vector consists of two electrodes (A and B) such as the RVcoil and case housing. The measured impedance is regarded under the near-field model as being the sum of the impedances associated with each of the electrodes. As noted above, this may be represented as:

Far-field Model: Impedance=A to B=Field between A and B

Near-field Model: Impedance=A+B=Near-Field A+Near-Field B

In FIG. 3A, the far-field model is shown via graph 108. The near-field model is shown via graph 109 (FIG. 3B), with local near-field contributions 110 and 111 specifically identified. The near-field concept is, however, not limited to a single pair of electrodes but is instead applicable to multi-polar vectors (e.g., tri-polar, quadripolar, etc.)

In FIG. 4A, the far-field model is shown via heart 112 and far-field zone 113. The near-field model is shown via heart 114 and local near-field zones 115 and 116 (FIG. 4B). For the example of a ring electrode of an RV lead, the relative near-field generally corresponds to a field localized within the right ventricle about 1-2 cm around the ring electrode (i.e., RV apex). For the device case electrode (not shown in FIG. 4), the relative near-field generally corresponds to a field localized within the entire device pocket. The near-field for the case is larger than for an individual lead ring or tip electrode because of the relatively larger surface area of the case electrode. As yet another example, for a ring electrode of an LV lead, the relative near-field is localized to the coronary vein and the adjacent LV myocardium/cavity and pericardial space. For a ring electrode of an RA lead, the near-field is localized within the right atrial appendage.

The near-field concept is not limited to pairs of electrodes. As shown in FIG. 5, the near-field model is applicable to more generalized embodiments such as those that relate "impedance triangle" measurements Z1, Z2 and Z3 made along three lead configuration vectors (A to C, A to B, and B to C) or more general "impedance polygonal" measurements. In FIG. 5, an impedance triangle model is shown via vector graph 117. Exemplary locations of three such electrodes within a patient are shown on the right via drawing 118. In this regard, an impedance triangle may be defined in which the impedance along each lead configuration vector can be related to the summation of the impedances associated with each of the three electrodes, and where the addition and subtraction of multiple vectors may be used to derive the impedance associated with an individual electrode. Note that the fluid volume around a given electrode is dependent on the degree of scar tissue formation and myocardial tissue surrounding and in contact with the electrode, along with the location of the implant site. The variability in the pattern of scar tissue and myocardial tissue around an electrode and its implant site produces a variable pattern of fluid washout around the electrode pair in combination with a variable pattern of electrode and surrounding tissue contact throughout the cardiac and respiratory cycles, such that the continuous impedance signal recorded during the cardiac and respiratory cycles on a beat-to-beat basis (i.e., the cardiogenic impedance Signal—CI) can vary significantly from patient to patient. Some typical electrodes (e.g. RVring, RVcoil, and RAring) generally have a high degree of variability, while others (LVring and Case) typically have a lower degree of variability from patient to patient. Using a vector such as LVring-LVtip typically simplifies the interpretation of CI waveform data because the electrodes are confined to a small space within the coronary vein where variations in fluid washout against the electrodes and implant site from patient to patient are likely to be less, but there still may be a contribution from the LV that depends on LV wall thickness and the pericardial space that depends on the extent of scar tissue present. In addition, deriving the impedance signal for a single cardiac electrode (e.g., LVring) tends to simplify the interpretation of the waveforms because the effects are isolated to a single electrode rather than multiple electrodes. This will be explained further below with reference to various examples where the near-field model allows physical phenomenon associated with particular electrodes to be easily identified, such as any electrodes that might be defective or which develop a disruption at the electrode-tissue interface.

Note also that the size of the near-field for each electrode depends on multiple factors, such as the physical size of the electrode, the materials used, the amount of contact with blood versus tissue, scar tissue thickness, ventricular wall thickness, etc. In general, the size of the near-field is larger for electrodes with larger surface areas, such as the device housing electrode or coil electrodes. Consider for example the following two impedance "triangles": (a) a triangle with small electrodes: RVring-LVring, LVring-RAring, RAring-RVring and (b) a triangle with large electrodes: RVcoil-Case, SVCcoil-Case, RVcoil-SVCcoil. The impedance associated with the smaller ring electrodes reflect phenomena occurring within tissues very close to the electrode, whereas the impedance associated with the larger case or coil electrodes reflect phenomena occurring within tissues both very close to the electrode and somewhat farther away from the electrodes. Both are deemed herein to be "relative" near-field phenomena so as to distinguish from true far-field phenomena. Based on experimental data and simulations, the size of the near-field is estimated to be within a close vicinity (<1 to 3 cm) of most electrodes. Otherwise routine experimentation can be employed to more precisely determine the size of the near-field surrounding any given electrode.

In view of these considerations, the term "near-field" as used herein should be interpreted as "relative near-field" since the exact size of the near-field associated with a given electrode depends on various factors. In some descriptions herein, the term "relative" is applied to near-field so as to remind the reader that the near-field impedances are near-field relative to far-field measurements, but it should be understood that, even in cases where the term "relative" is not specifically used, "relative near-field" is intended. It should also be noted that if the electrodes of a given pair are very close to one another there could be overlap between the near-field of one electrode and the near-field of the other.

As explained above, aspects of the invention are generally and broadly applicable to either bipolar impedance or quadripolar impedance. In this regard, for a quadripole example where three current electrodes A, B and C are used along with three voltage electrodes D, E and F (that are not in close proximity to corresponding current electrodes), a set of linear equations can be solved for D, E and F, though the interpretation of the results may be unclear, particularly from a clinical standpoint. For a quadripole example where A and D are in close proximity to one another (i.e. within each other's relative near-fields), where B and E are in close proximity, and where C and F are in close proximity, then the quadripolar impedance reduces to a bipolar impedance and the clinical interpretation of the resulting near-field impedances is as discussed herein below. Hence, the techniques described herein are primarily intended to be practiced for use with bipolar impedance or for use in quadripolar cases where the current and voltage nodes are in close proximity to one another, which is typically the case for tip/ring pairs. For example, the RVtip and RVring electrodes are typically in close proximity such that they are within each other's relative near field.

Exemplary Near-Field Impedance-Based Assessment Techniques

Figure 6:
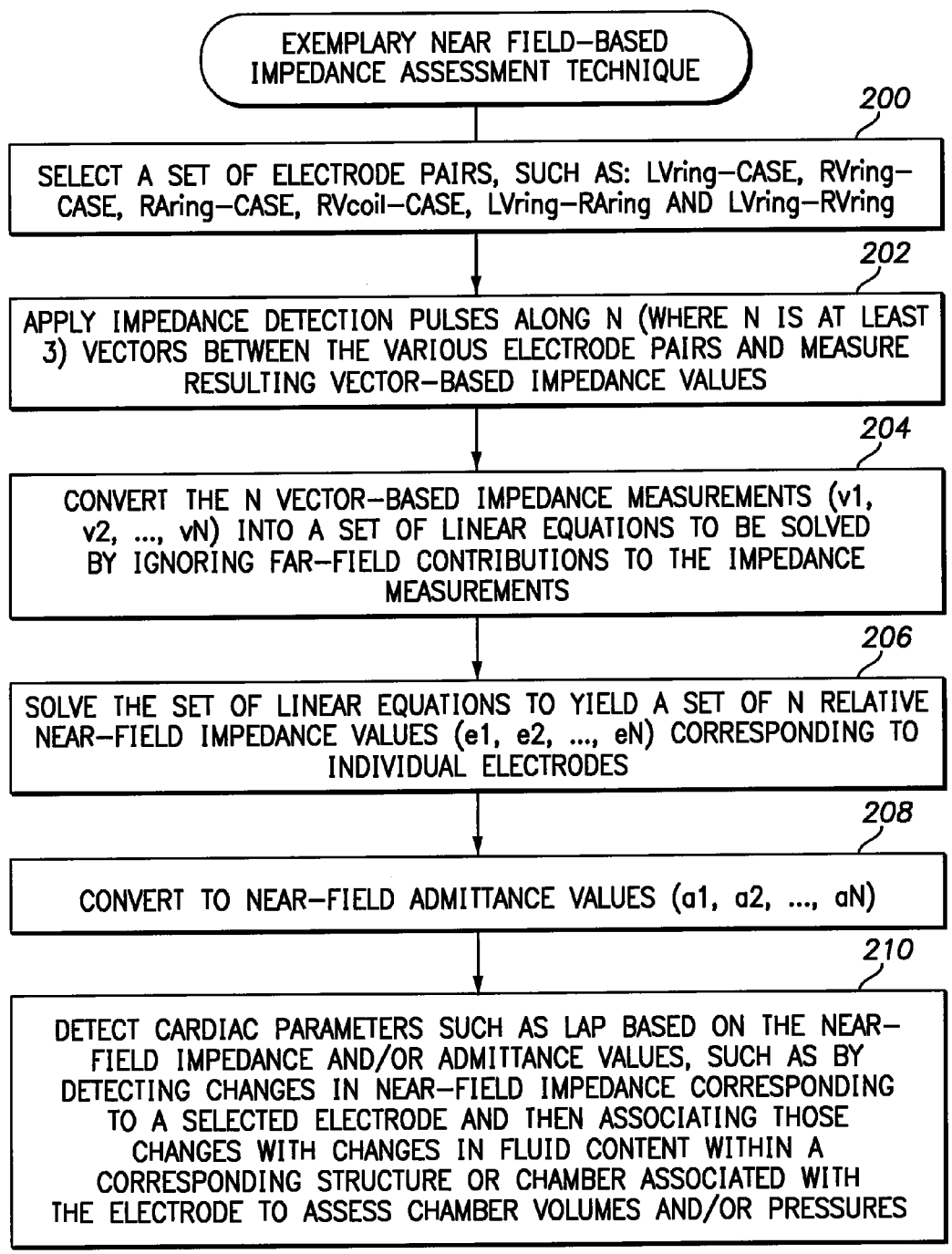
FIG. 6 illustrates an exemplary method performed in accordance with the general technique of FIG. 2, wherein N linear equations are exploited to determine N near-field impedance values from vector-based impedance measurements.

Referring next to FIG. 6, illustrative techniques will be described that exploit the near-field model in connection with an example wherein vector-based impedance is initially detected. Beginning at step 200, the pacer/ICD selects a set of electrode pairs from among a set of available electrodes of an implanted lead system, such as the set consisting of: LVring-case, RVring-case, RAring-case, RVcoil-case, LVring-RAring and LVring-RVring. For a case where there are N individual electrodes, the device, at step 202, applies impedance detection pulses along N vectors (where N is at least 3) between the various electrode pairs and measures N resulting vector-based impedance values. (Note that, although it is sufficient for the device to acquire measurements along N vectors to derive the near-field impedance measurements associated with N electrodes, a greater number of vectors can be used, such as N+1, to determine the near-field impedances of the N electrodes. The use of more vectors (such as N+1) than electrodes (N) can be exploited to validate the solution for N.)

The impedance signals are obtained by transmitting electrical current between a pair of electrodes and subsequently measuring the voltage between the same or another pair of electrodes. The impedance may be calculated as the ratio of the measured voltage to the transmitted current. In some examples, a tri-phasic impedance pulse waveform is employed to sense the impedance signal. The tri-phasic waveform is a frequency-rich, low energy waveform that provides a net-zero charge and a net-zero voltage. An exemplary triphasic pulse waveform is described in detail in U.S. patent application Ser. No. 11/558,194, of Panescu et al., filed Nov. 9, 2006, entitled "Closed-Loop Adaptive Adjustment of Pacing Therapy based on Cardiogenic Impedance Signals Detected by an Implantable Medical Device."

At step 204, the device converts the vector-based impedance measurements (v1, v2, . . . , vN) into a set of linear equations to be solved by ignoring far-field contributions to the impedance measurements. That is, the device exploits the near-field model by recognizing that far-field contributions can be advantageously ignored. At step 206, the device then solves the set of linear equations to yield a set of N near-field impedance values (e1, e2, . . . , eN) corresponding to the N individual electrodes. At step 208, the device converts the near-field impedance values to near-field admittance values (a1, a2, . . . , aN) by, for example, taking the reciprocal of each. At step 210, the device then detects cardiac parameters such as LAP based on the near-field admittance values (or on the near-field impedance values), such as by detecting changes in near-field impedance corresponding to a selected electrode and then associating those changes with changes in fluid content within a corresponding structure or chamber associated with the electrode to assess chamber volumes and/or pressures.

As noted, the relative near-field impedance/admittance value for each electrode generally corresponds to the fluid volume surrounding the electrode. Each electrode can be associated with a specific location within the heart or subcutaneous tissues. The clinical importance of this association between each electrode and one corresponding anatomical location/structure is that it becomes straight-forward to interpret any changes that occur within the electrode impedance measurements. This is because a change observed in the impedance associated with a given electrode (e.g., LVring) may then be used to indicate a change in fluid content within the corresponding location/structure (e.g., coronary vein/LV myocardium or cavity/pericardial space). Such a one-to-one association cannot readily be made when interpreting measurements of vector-based impedance values because each vector measurement reflects a combination of events occurring among the various electrodes that comprise the vector.

Figure 7:
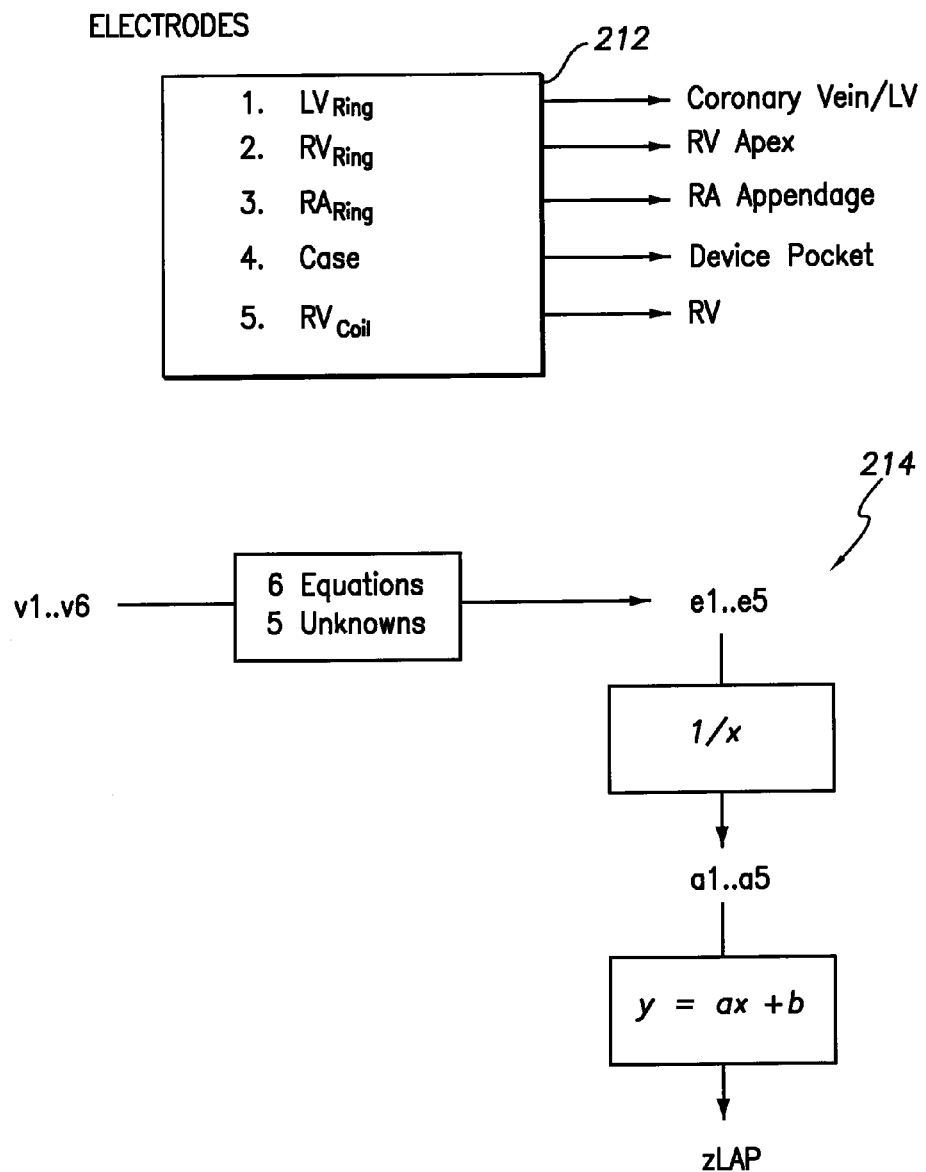
FIG. 7 is a schematic diagram illustrating aspects of the procedure of FIG. 6 for an example where six vectors are used to assess five impedance values, and particularly illustrating the estimation of LAP from near-field admittance.

FIG. 7 schematically illustrates the exemplary procedure of FIG. 6 applied to an example where six impedance vectors are measured to determine the near-field impedances of five electrodes. That is, FIG. 7 illustrates an example where N+1 vectors are used to determine N near-field impedance values. Block 212 summarizes the relationship between particular electrodes and the corresponding structures to which the near-field impedance values relate. The association between each electrode and the anatomical structure shown is for illustrative purposes and is not intended to be restrictive in any way. For example, the LVring electrode may be associated with the adjacent coronary vein, LV myocardium and cavity, and the pericardial space. Similarly, the RVring electrode may be associated with the adjacent RV apex/cavity, the RV septum/cavity, RV outflow tract/cavity depending on the chosen implant site. Flow diagram 214 schematically summarizes the conversion of vector-based impedance measurements (for an example with five electrodes) into near-field impedance values, and then to near-field admittance values, and ultimately to estimated LAP values based, in this particular example, on a linear correlation.

FIG. 8 summarizes the conversion of a set of six exemplary vector-based impedance measurements 216 into five individual electrode near-field values via matrix inversion formulae 218. The solution in matrix form 219 is also provided in the figure.

Figure 9:
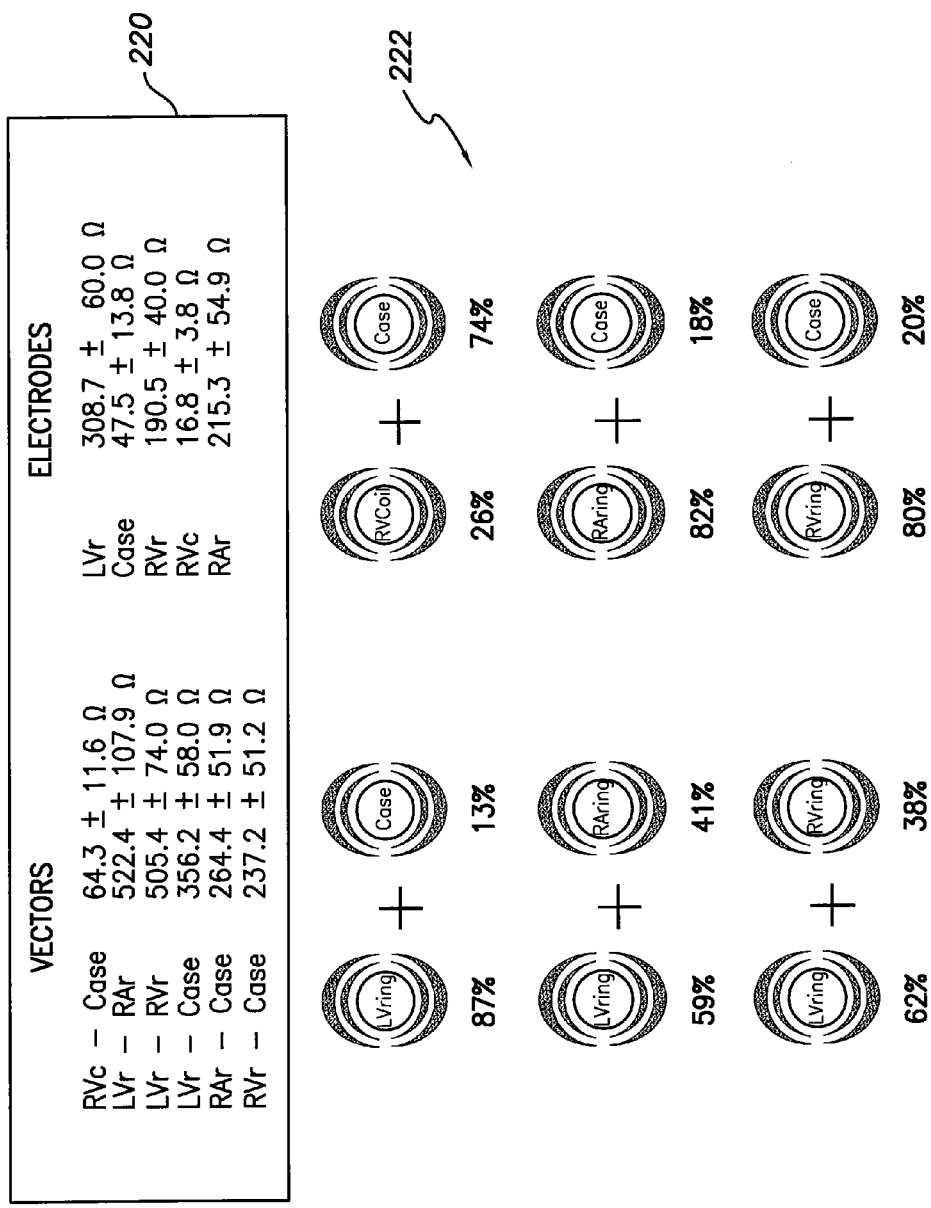
FIG. 9 is a diagram illustrating exemplary near-field impedance values calculated by the procedure of FIG. 6, and particularly illustrating the various near-field contributions to initial vector-based impedance measurements.

FIG. 9 provides exemplary values for the vector-based impedances and the corresponding near-field impedances by way of chart 220 derived from the analysis of data from human subjects. Take, for example, the vector-based impedance of the RVcoil—case pair, which is shown to be about 64.3 ohms. Under the near-field model, this is formed from the combination of the RVcoil impedance (about 16.8 ohms) plus the case impedance (about 47.5 ohms), which when added together provide the full 64.3 ohms of pair-based impedance. The figure additionally illustrates the relative distribution of impedance between pairs of electrodes via graph 222. For example, for the LVring/case electrode pair, the majority of impedance (87%) is associated with the LVring and only 13% is associated with the case. As such, a pair-based impedance measurement along that vector primarily captures the impedance near the LVring rather than near the case (or in the far-field region therebetween.) The LVring contributes more impedance than the case because of the smaller surface area associated with the LVring at the electrode-tissue interface in comparison to the Case electrode. As another example, for the LVring/RAring electrode pair, the amount of impedance associated with the LVring (59%) is of the same order of magnitude as the impedance associated with RAring (41%.) There is comparatively little difference between the LVring and the RAring near-field impedances in this example because both have similar electrode sizes. The relative contributions to vector-based impedance illustrated within FIG. 9 represent just one type of useful data that can be obtained by deriving and analyzing near-field impedances.

Figures 1, 10:
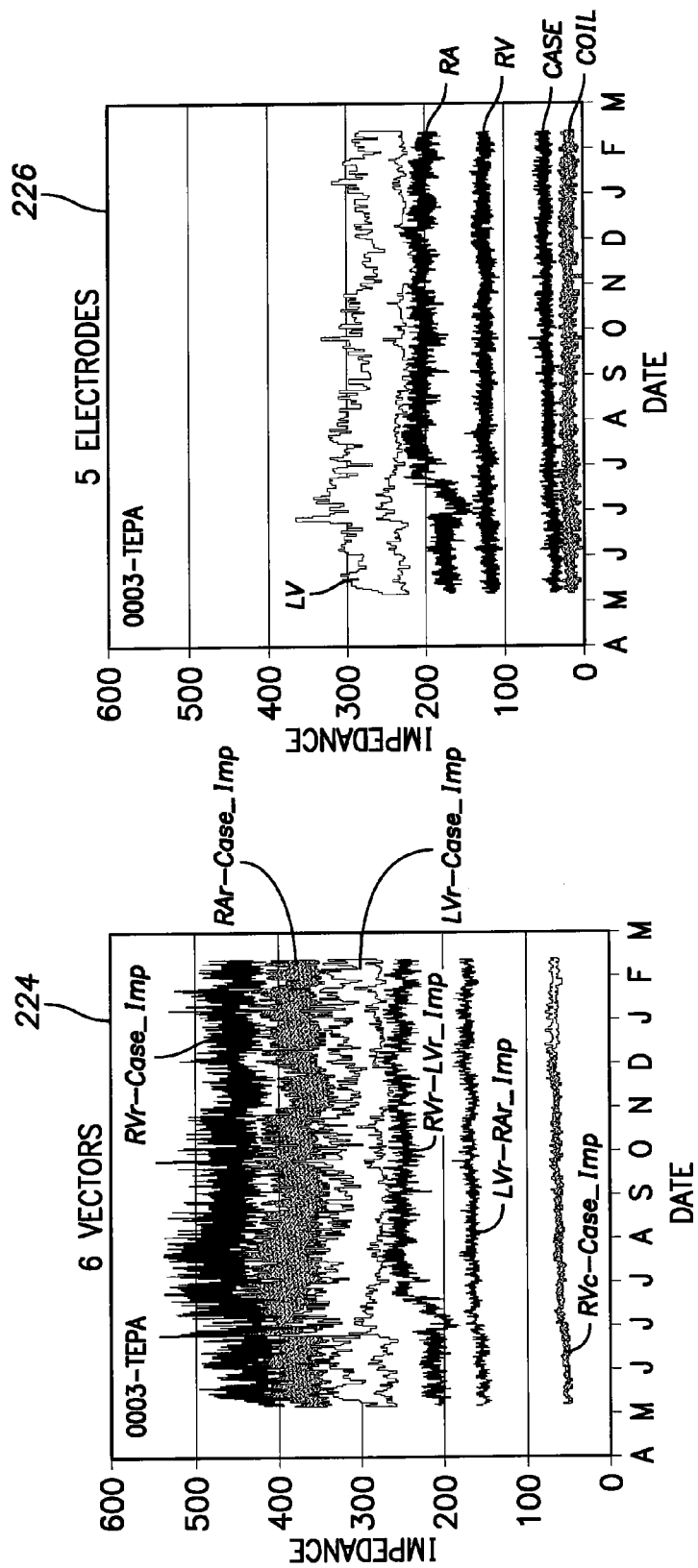
FIG. 10 provides exemplary graphs corresponding to data that can be processed by the procedure of FIG. 6, which particularly illustrate time-varying changes in various near-field impedance or admittance signals derived from vector-based impedance measurements.
Figures 3, 10:
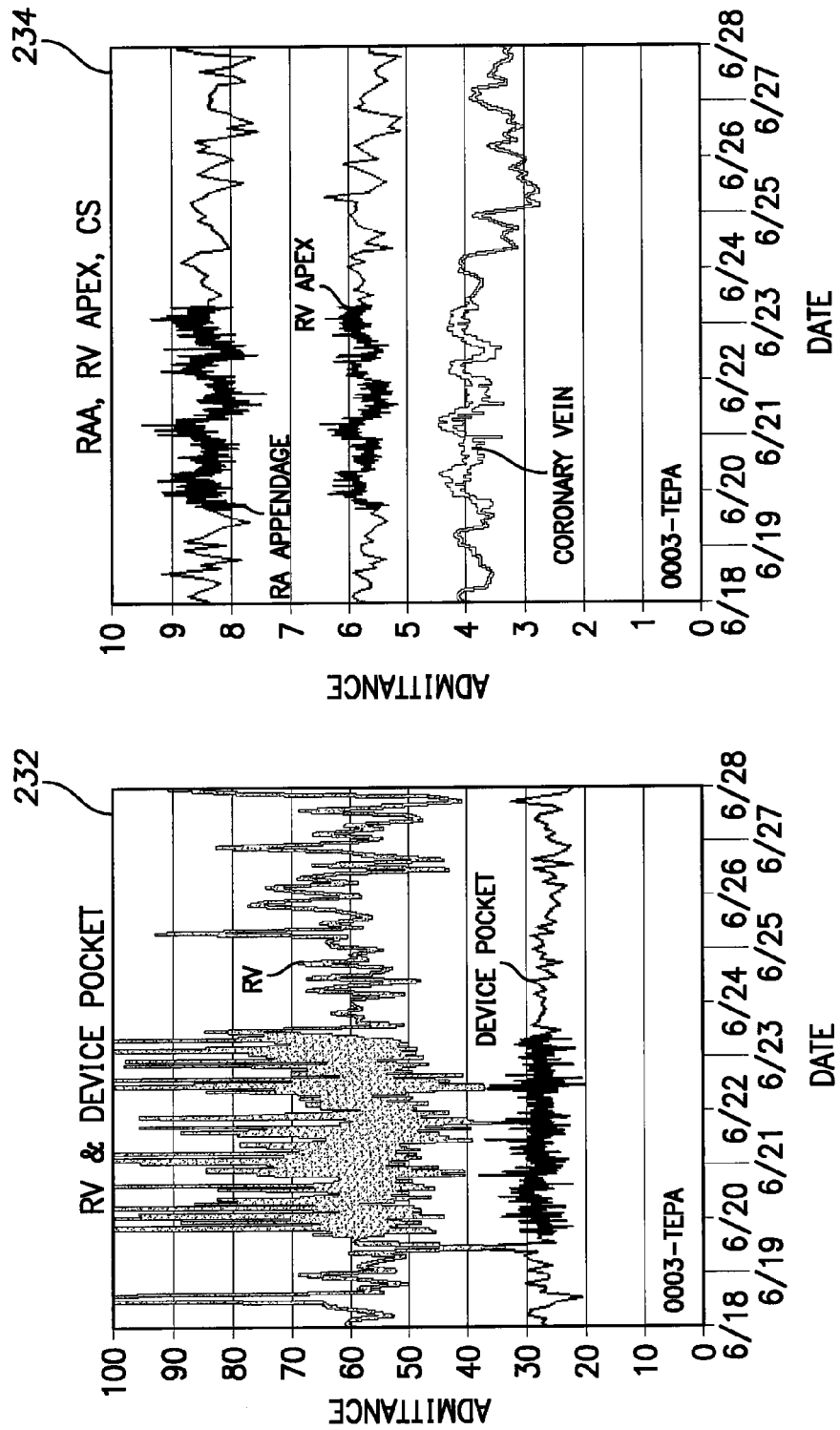

FIG. 10 illustrates time-varying changes in near-field impedance/admittance signals corresponding to various combinations of the individual electrodes from an exemplary human test subject. Referring first to graphs 224 and 226, the relative contribution of each of the electrodes toward each impedance vector can easily be seen as tracked over time. For example, for the LVring/Case vector, the LVring electrode has a near-field impedance of about 250 ohms, whereas the case electrode has a near-field impedance of about 50 ohms. Thus, the majority of the impedance for this vector is associated with the LVring electrode (250/300=83%). For the RVcoil/case vector, the RVcoil has a near-field impedance of about 20 ohms, while the case electrode has a near-field impedance of about 50 ohms. Thus, the majority of the impedance for this vector is associated with the case electrode (50/70=71%).

The accumulation of fluid around the RVring and the case electrodes will have different time constants associated with the response to an increase in intravascular fluid volume. An increase in the intravascular fluid volume produces a fast increase in RV volume, which produces a corresponding fast change in the near-field impedance associated with the RVring electrode. The increase in RV volume also produces a corresponding change in the interstitial fluid volume within the subcutaneous device pocket, which produces a change in the near-field impedance associated with the Case electrode. However, the change in the interstitial fluid volume within the device pocket occurs much slower relative to the change in RV volume, such that the change in the near-field impedance for the Case electrode occurs slower than change seen for the RVring electrode.

As already explained, the near-field impedances determined for each of the electrodes can be transformed into near-field admittance values to provide an assessment of fluid volume content surrounding the electrode. Variable times to electrode stabilization (due to scar tissue maturation) following implant can be seen for the various electrodes. In addition, it can be seen that the RVcoil electrode corresponding to the fluid volume content within the RV cavity has large magnitude variations (i.e. it is noisy). This is particularly illustrated by way of graphs 228 and 230, especially the noisy admittance signal of RV admittance in graph 228. The importance of this observation is that a vector comprising of the RVcoil and Case electrodes (RVcoil-Case) essentially only provides useful information from the Case electrode (i.e., Device Pocket) since the RVcoil electrode is too noisy to provide any clinically useful information.

Referring next to graphs 232 and 234 of FIG. 10, a higher sampling rate over a ten day interval shows that the LVring electrode in this example has an excellent signal to noise ratio with clear diurnal variations that may be useful for impedance-based LAP estimate calibration (i.e. zLAP calibration.) This diurnal transformation permits a zLAP estimation via a linear function (e.g. zLAP=Gain*Admittance+Offset), which is discussed more fully below with reference to FIG. 19. The diurnal variations seen for the various electrodes are reflective of variations in fluid distribution occurring within the vicinity of each electrode in response to fluid shifts that occur following changes in posture.

Exemplary Near-Field Model-Based Applications

Figure 11:
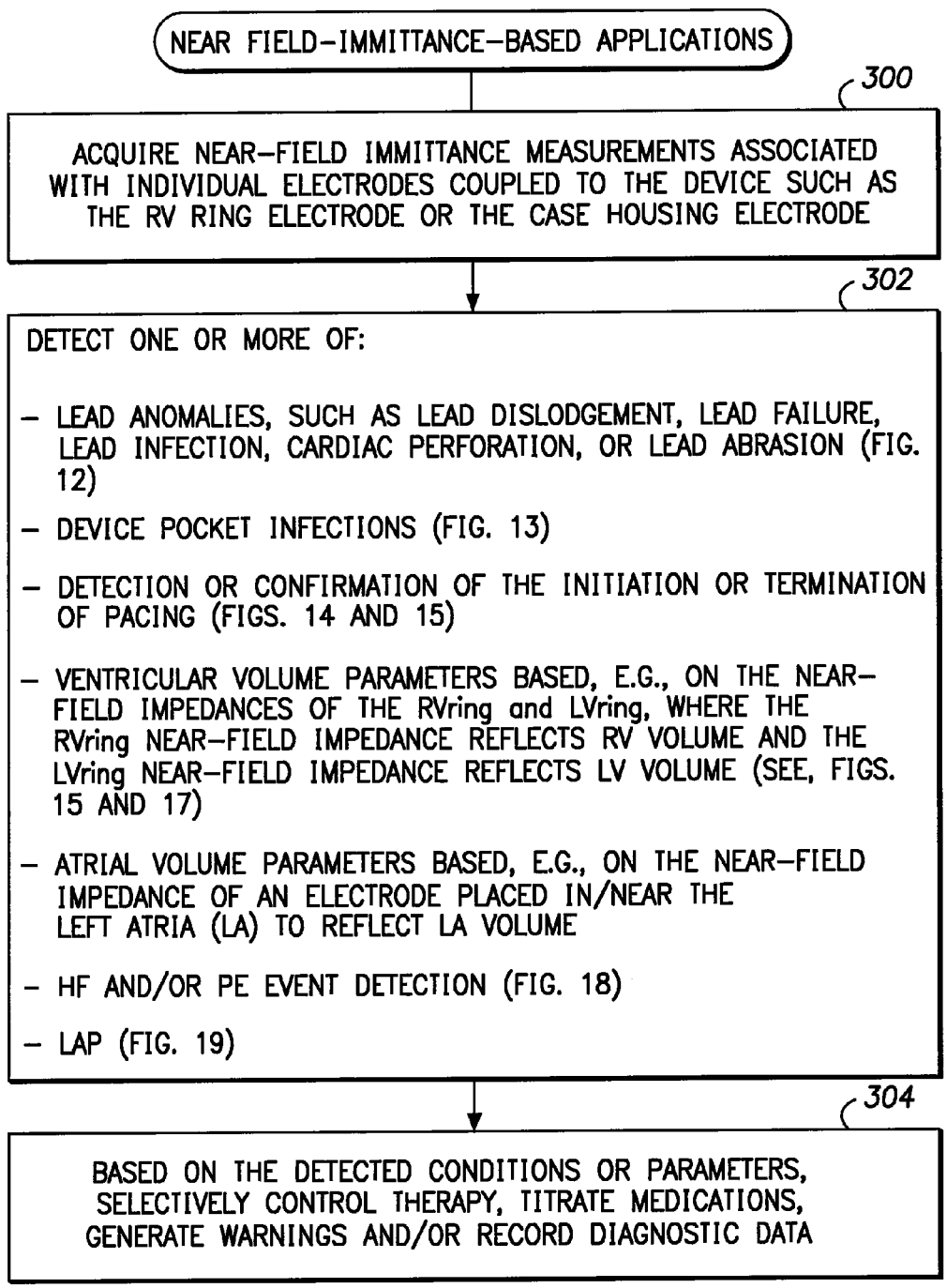
FIG. 11 is flow chart illustrating exemplary applications of the general technique of FIG. 2 wherein near-field impedance measurements associated with particular electrodes are exploited to detect various conditions or parameters, such as to detect lead anomalies or to estimate LAP.

FIG. 11 summarizes various applications that exploit near-field impedance or admittance values associated with various electrodes. Beginning at step 300, the pacer/ICD acquires near-field immittance measurements (i.e. near-field impedance or admittance values) associated with individual electrodes coupled to the device, such as the RV ring electrode or the case housing electrode. (These near-field values may be obtained using the techniques of FIGS. 6-8, discussed above.) At step 302, the device then detects one or more of:
  lead anomalies, such as lead dislodgement, lead failure, lead infection, cardiac perforation, or lead abrasion (see, FIG. 12);
  device pocket infections (see, FIG. 13);
  confirmation of the initiation or termination of pacing (see, FIGS. 14 and 15);
  Ventricular volume parameters based, e.g., on the near-field impedances of the RVring and the LVring, where the RVring near-field impedance reflects RV volume and the LVring near-field impedance reflects LV volume (see, FIGS. 16 and 17)
  Atrial volume parameters based, e.g., on the near-field impedance of an electrode placed in/near the left atria (LA) to reflect LA volume;
  HF and/or PE events (see, FIG. 18); and
  LAP (see, FIG. 19).
At step 304, based on the detected conditions or parameters, the device then selectively controls therapy, titrates medications, generates warnings and/or records diagnostic data. For example, in the case of lead anomalies or pocket infections, warnings are preferably generated to warn the clinician of the problem so that the issue can be addressed.

Figure 12:
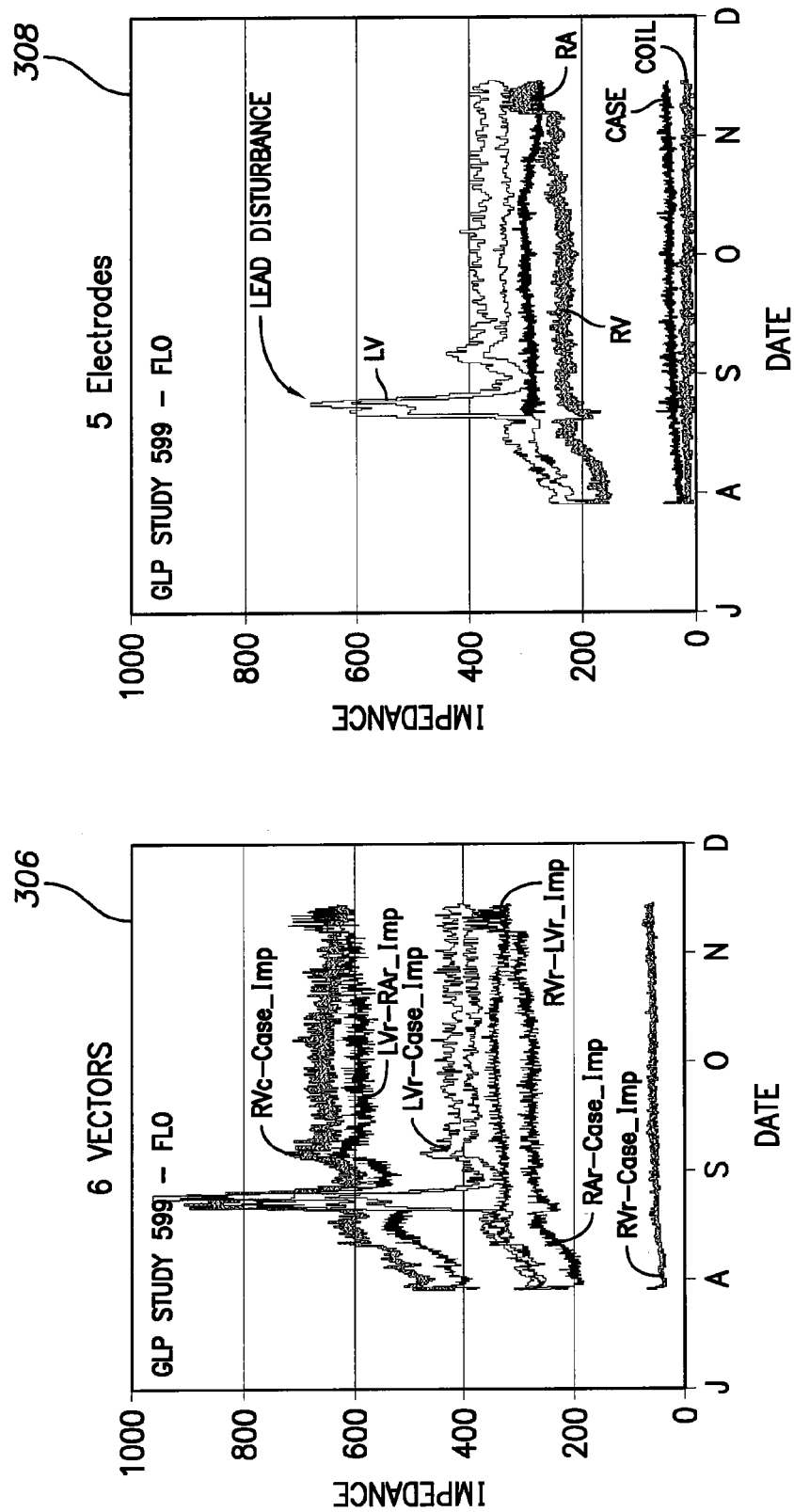
FIG. 12 provides exemplary graphs corresponding to data that can be processed by the procedure of FIG. 11 to detect lead anomalies, which particularly illustrate time-varying changes in various near-field impedance signals representative of a temporary lead disturbance.

FIG. 12 provides exemplary time-varying impedance signals that illustrate a lead disturbance. More specifically, a first graph 306 illustrates vector-based impedance signals for an animal model wherein a disturbance in the LV lead has been introduced. A second graph 308 illustrates near-field impedance values associated with the individual electrodes. As can be seen, when examining the near-field impedances of graph 308, it is immediately clear that the disturbance is within the LV lead; whereas when examining the vector-based impedances of graph 306, the source of the disturbance is not easily ascertained. That is, when attempting to detect and isolate lead disturbances using vector-based impedance vectors, the particular lead is not readily identified because the disturbance may affect more than one vector depending on how many vectors utilize the same electrode or the same lead. The near-field immittance measurements derived for each electrode are useful for detecting other lead anomalies, which include but not limited to lead dislodgement, lead failure (e.g., lead fracture), lead infection, lead abrasion, and/or lead perforation.

Figure 13:
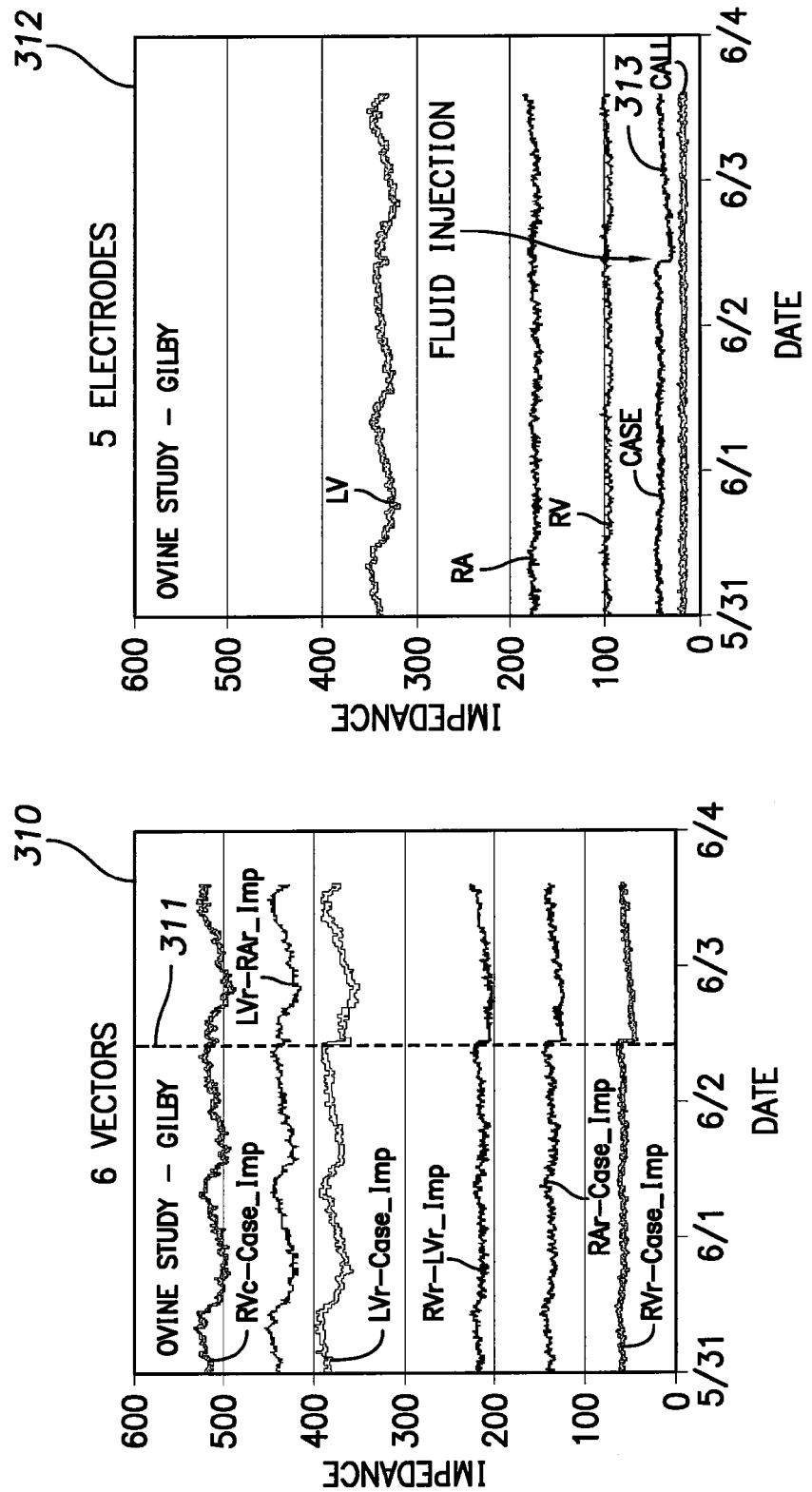
FIG. 13 provides exemplary graphs corresponding to data that can be processed by the procedure of FIG. 11 to detect pocket infections, which particularly illustrate time-varying changes in various near-field impedance signals representative of fluid injection intended to emulate a device pocket infection.

FIG. 13 provides exemplary time-varying impedance signals that illustrate affects caused by a pocket infection emulated via the injection of fluids into the tissue pocket surrounding an implanted device of an animal test subject. A first graph 310 illustrates vector-based impedance signals derived from an ovine test subject in which liquid was injected into the device pocket at time 311 to emulate a pocket infection. A second graph 312 illustrates near-field impedance values associated with the individual electrodes, including a case electrode near-field impedance trace 313. When examining the near-field impedances of graph 312, particularly trace 313, it is immediately clear that there is sudden drop in impedance near the device housing (case) electrode indicative of a possible pocket infection of the type where fluids containing inflammatory and white blood cells surround the device in response to the infection. However, when examining the vector-based impedances of graph 310, the source of the disturbance in impedance is not easily ascertained as it affects several of the traces. It is noted that the fluid was subsequently reabsorbed over the next twenty-four hour period following its introduction, causing the near-field impedance of the device case to return to its prior baseline level.

Figure 14:
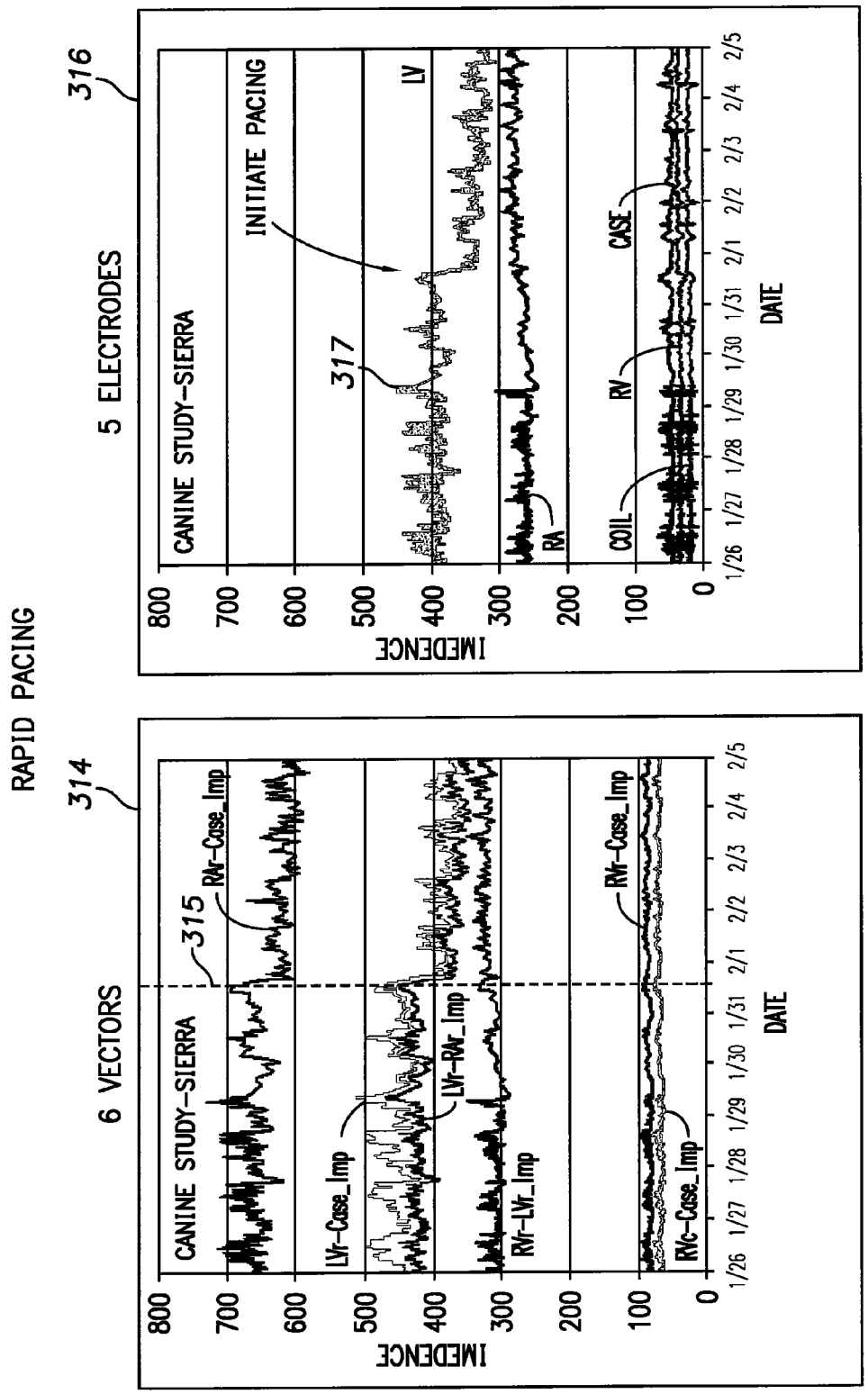
FIG. 14 provides exemplary graphs corresponding to data that can be processed by the procedure of FIG. 11 to confirm the initiation or termination of pacing, which particularly illustrate time-varying changes in various near-field impedance signals representative of the initiation of rapid pacing.

FIG. 14 provides exemplary time-varying impedance signals that illustrate impedance affects occurring due to the initiation of rapid ventricular pacing within an animal test subject. More specifically, a first graph 314 illustrates vector-based impedance signals derived from a canine test subject in which rapid pacing was initiated at time 315. Such pacing has the effect of acutely increasing LAP, which causes a corresponding decrease in various vector-based impedance values as shown (and which may be due, in part, to a sudden increase in LV volume.) A second graph 316 illustrates near-field impedance values associated with the individual electrodes, including an LV electrode near-field impedance trace 317. When examining the near-field impedances of graph 316, particularly trace 317, it is immediately clear that there is sudden drop in impedance in or near the LV; whereas when examining the vector-based impedances of graph 314, the source of the disturbance in impedance is not easily ascertained.

Following a prolonged period of rapid ventricular pacing (four to eight weeks) in the canine test subject, a gradual increase in LV volume is expected that coincides with an increase in LAP. Upon cessation in rapid ventricular pacing, an acute decrease in LAP is expected to occur as a result of the elimination of cannon A-waves. However, a corresponding slower change (i.e. a lag) in the impedance associated with the LVring electrode occurs as the LV volume returns over the subsequent weeks toward baseline. This produces a hysteresis-like behavior between LAP and LV volume. This hysteresis behavior is described more fully in co-pending U.S. patent application Ser. No. 12/853,157, filed concurrently herewith, of Gutfinger et al., entitled "Systems and Methods for Estimating Left Atrial Pressure (LAP) in Patients with Acute Mitral Valve Regurgitation for Use by an Implantable Medical Device," which is fully incorporated by reference herein.

Figure 15:
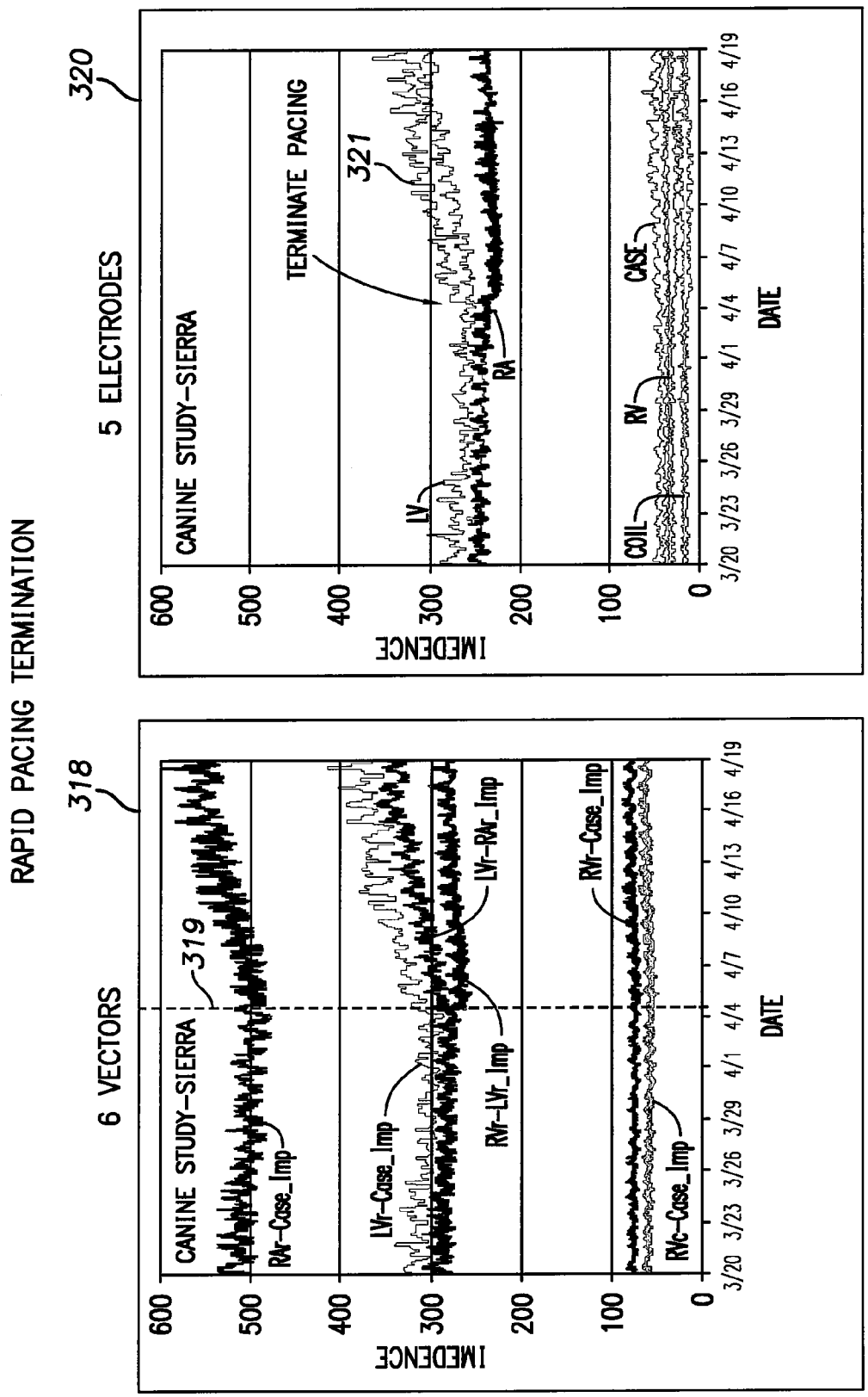
FIG. 15 provides exemplary graphs corresponding to data that can be processed by the procedure of FIG. 11 to detect the initiation or termination of rapid pacing, which particularly illustrate time-varying changes in various near-field impedance signals representative of the termination of rapid pacing.

FIG. 15 illustrates the changes in impedance occurring within the canine test subject following cessation of rapid pacing by way of vector-based impedance graph 318 and near-field impedance graph 320. Rapid pacing was terminated at time 319 and subsequent increases in impedance are then observed in several of the pair-based impedance traces of graph 318, but most significantly in the LV trace of the near-field impedances.

Thus, FIGS. 14-15 show that the initiation and termination of rapid ventricular pacing that are associated with acute physiologic changes in pressure and intra-cardiac volume can be readily detected and identified within near-field impedances.

FIG. 16 illustrates LV EDV and LAP. A first graph 322 shows a linear relationship 324 between near-field admittance of the LV ring electrode and LV EDV. Based on this relationship, the device converts near-field LVring admittance values obtained by the device into LV EDV values. In this regard, by decomposing vector-based impedance vector measurements into near-field values, an indication of LV volume may be obtained using the ring electrode of the LV lead. In one example, a non-invasive echocardiogram study with simultaneous acquisition of impedance signals is used to determine LV EDV and LV ESV values for the patient along with the corresponding impedance measurements. Impedance signals are acquired at a high sampling rate (e.g., 128 Hz) along three lead configuration vectors that form an impedance triangle (e.g., LVring-Case, RVring-LVring, and RVring-Case). The near-field impedance signal associated with the LV ring electrode is derived and used to determine the minimum and maximum near-field impedance measurements for the LV ring electrode within each cardiac cycle, which are then averaged over multiple cardiac cycles to yield a representative maximum and minimum impedance measurement (Zmin and Zmax). Zmin and Zmax are then converted to corresponding near-field admittance measurements that are calibrated to match the LV volume measurements for the patient obtained via the echocardiogram. The impedance associated with the LVring electrode is then used by the implanted device to estimate LV volumes (zVolume) for the patient.

A second graph 325 shows a relationship 327 between LAP and LV EDV that can be characterized using an exponential formula, a polynomial formula or other transformational model or formula. Based on this relationship, the device converts the LV EDV values into LAP values. Estimates of LV EDP or LAP can then be derived. The RV volume can similarly be derived by correlating RV admittance with RV EDV and RV ESV. Beat-to-beat variations with knowledge of ejection fraction (EF) and stroke volume may also be used to calibrate the data.

FIG. 16 includes a graph 325 and equations relating LV EDV to LAP. The relationship between LV EDV and LAP may be non-linear (e.g., exponential), but for practical purposes be modeled with a linear equation over a narrow range of filling volumes and pressures. The relationship between LV EDV and LAP may be determined for each patient individually with use of an echocardiogram to assess LV EDV and the use of a pulmonary capillary wedge pressure measurement obtained using a pulmonary artery catheter to assess LAP. An estimate of LAP based on impedance (zLAP) may subsequently be derived by transforming the previously derived zVolume estimate obtained from the near-field impedance associated with the LV ring electrode into a corresponding LAP estimate. Impedance-based LAP estimation is generally referred to herein as "zLAP." Prior zLAP techniques are discussed in U.S. patent application Ser. No. 11/559,235, filed Nov. 13, 2006, entitled "System and Method for Estimating Cardiac Pressure Using Parameters Derived from Impedance Signals Detected by an Implantable Medical Device", as well as in at least some of the following applications: U.S. Provisional Patent Application No. 60/787,884, filed Mar. 31, 2006 entitled "Tissue Characterization Using Intracardiac Impedances with an Implantable Lead System." See, also, U.S. patent application Ser. Nos. 11/558,101, filed Nov. 9, 2006; 11/557,851, filed Nov. 8, 2006; 11/557,870, filed Nov. 8, 2006; 11/557,882, filed Nov. 8, 2006; and 11/558,088, filed Nov. 9, 2006; each entitled "Systems and Methods to Monitor and Treat Heart Failure Conditions."

Insofar as the choice of the LVring electrode, the LVring near-field impedance is believed to provide the best correlation with LAP and with LV EDV. In this regard, the LVring near-field impedance appears to provide a measure of myocardial and surrounding tissue conductivity in the field near the LVring electrode. The myocardial and surrounding tissue conductivity is affected by multiple factors, which include tissue characteristics/components/composition (muscle, scar, fat, blood) and can vary within the cardiac and respiratory cycles as blood flow within the myocardium changes and muscle thickening and relaxation takes place. Additional factors such as local edema within the myocardium in response to cell injury and leakage from the local vascular beds and/or adjacent fluid within the surrounding pericardial space and tissues can also affect the near-field impedance measurements. The beat-to-beat myocardial wall displacement and contractile strength can produce large magnitude changes within each cardiac cycle in myocardial conductivity in combination with changes in electrode-tissue contact as contractility and displacements/ejection fraction increase. Changes in myocardial conductivity and electrode-tissue contact can also vary with the respiratory cycle. As myocardial contractility decreases, there is less thickening in the myocardial wall with each contraction, causing LV volumes to increase and myocardial conductivity to increase secondary to the reduced thickening and reduced clearance of myocardial blood. Thus, at least in an indirect way, myocardial tissue conductivity reflects and correlates with LV volume, such that an inverse relationship exists between the near-field impedance associated with the LVring electrode and LV EDV. Since LV EDV correlates with LAP, LVring near-field impedance thereby also correlates with LAP.

Although the LVring is preferred, an electrode placed within or very close to the left atrium (e.g., within the coronary sinus) may similarly be used to correlate with Left Atrial (LA) volume and LAP. Still further, note that the RVring near-field impedance has an inverse correlation with RV volume. Beat-to-beat variations between min and max near-field impedance correlate inversely with RV EDV and RV ESV, allowing RV EDV and RV ESV to be estimated based on near-field RVring values.

Figure 17:
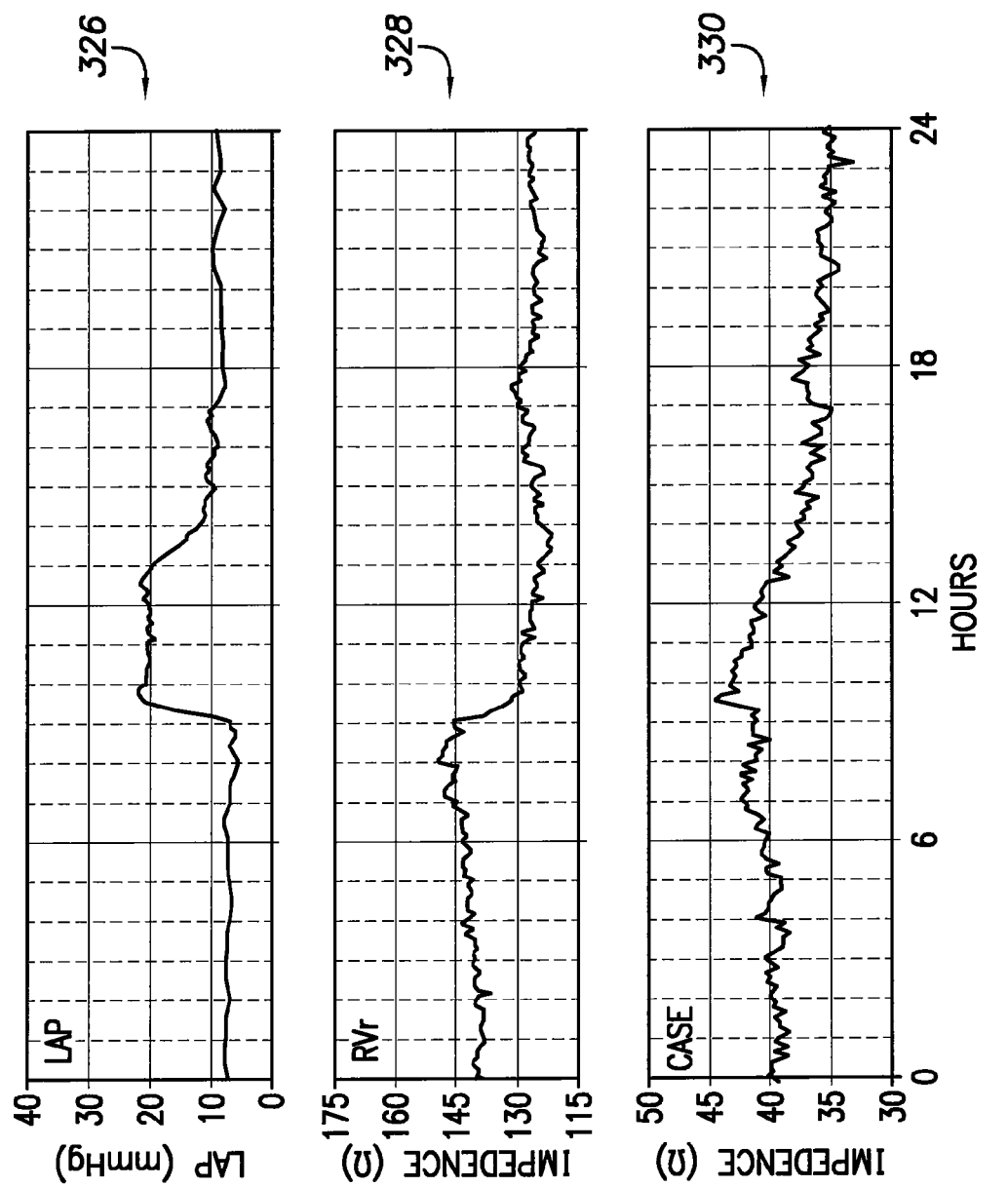
FIG. 17 provides exemplary LAP and impedance graphs corresponding to data that can be processed by the procedure of FIG. 11 to detect changes in fluid volume, which particularly illustrate time-varying changes in various near-field impedance signals representative of an increasing fluid volume status.

FIG. 17 provides a set of graphs of the LAP and near-field impedance associated with the RVring (or RVr) and Case electrodes derived from an ovine study during an acute volume loading experiment. The top graph 326 shows the measured LAP recorded over a time interval of twenty-four hours. Nine hours into the recording, four liters of a colloid solution was administered intravenously over a period of four hours (infusion rate of 1 Liter/hour). In response to acute fluid loading, the LAP increases from a baseline of about 8 mmHg to a peak of 20 mmHg over the first hour. Over the same time course, the administered fluid produces an acute decrease in the near-field impedance of the RVring electrode from 145 to 130 ohms, as shown by way of graph 328. During the next three hours, LAP remains stable at 20 mmHg, while the RVring electrode continues to decrease slightly from 130 to 125 ohms. In contrast to the near-field impedance associated with the RVring electrode, the near-field impedance associated with the Case electrode has a slower time course of response, as shown by way of graph 330. The near-field impedance associated with the case electrode decreases from a peak of 45 ohms to a minimum of 35 ohms over a period of 8 hours. The data also shows differences in the rate of recovery once the fluids are no longer administered. LAP recovers within an hour to a new baseline of 10 mmHg, while the recovery in the near-field impedances for both the RVring and Case electrodes is more subtle and over a longer duration. This difference may be a consequence of impedance reflecting more so a fluid volume rather than a pressure.

Figure 18:
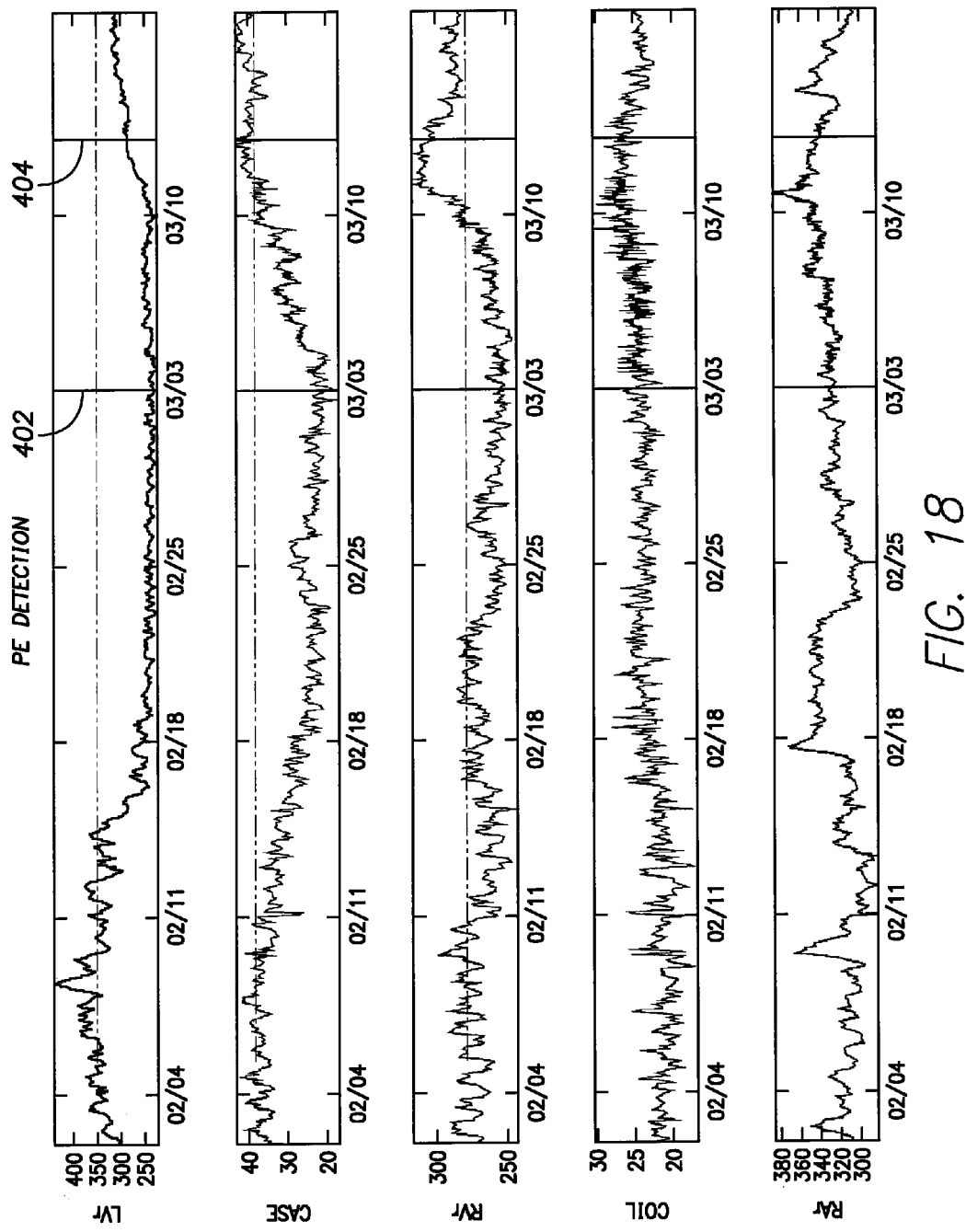
FIG. 18 provides exemplary impedance graphs corresponding to data that can be processed by the procedure of FIG. 11 to detect PE, which particularly illustrate time-varying changes in various near-field impedance signals representative of a PE event.

FIG. 18 provides a set of graphs 400 of near-field impedance traces leading up to cardiogenic PE event (i.e. an episode of acute pulmonary edema) within a patient. The actual episode of acute PE (which necessitated hospitalization) extends from time 402 to time 404. As can be seen, the various individual near-field admittance traces exhibit differing degrees of change prior to the PE event indicative of worsening cardiac condition. In particular, note that near-field impedance associated with the LVring exhibits a marked decrease in value well before the PE event, indicative of changes in LV volume. In this regard, LVring near-field admittance is believed to reflect LV volume and hence changes in LVring admittance reflect changes in LV volume, which can arise due to HF leading to acute PE. One advantage of examining the LVring near-field admittance is that there is little or no lag relative to LV volume, as might occur when examining pair-based impedance traces or other proxies for LV volume. In addition, the lag relative to changes in LAP is secondary to volume changing slower than pressure. The LV ring near-field admittance is less prone to far-field effects (e.g., pneumonia-based effects). It is noted that the strength of correlation between LV ring near-field admittance and LV volume can depend on multiple factors including: implant position, scar tissue formation, LV wall thickness, and the presence of pericardial fluid. Acute changes in LV ring near-field admittance also relate to LV compliance and ejection fraction (EF), providing an opportunity to assess compliance and EF within the patient.

Exemplary Near-Field Admittance-Based zLAP Estimation Technique

Figure 19:
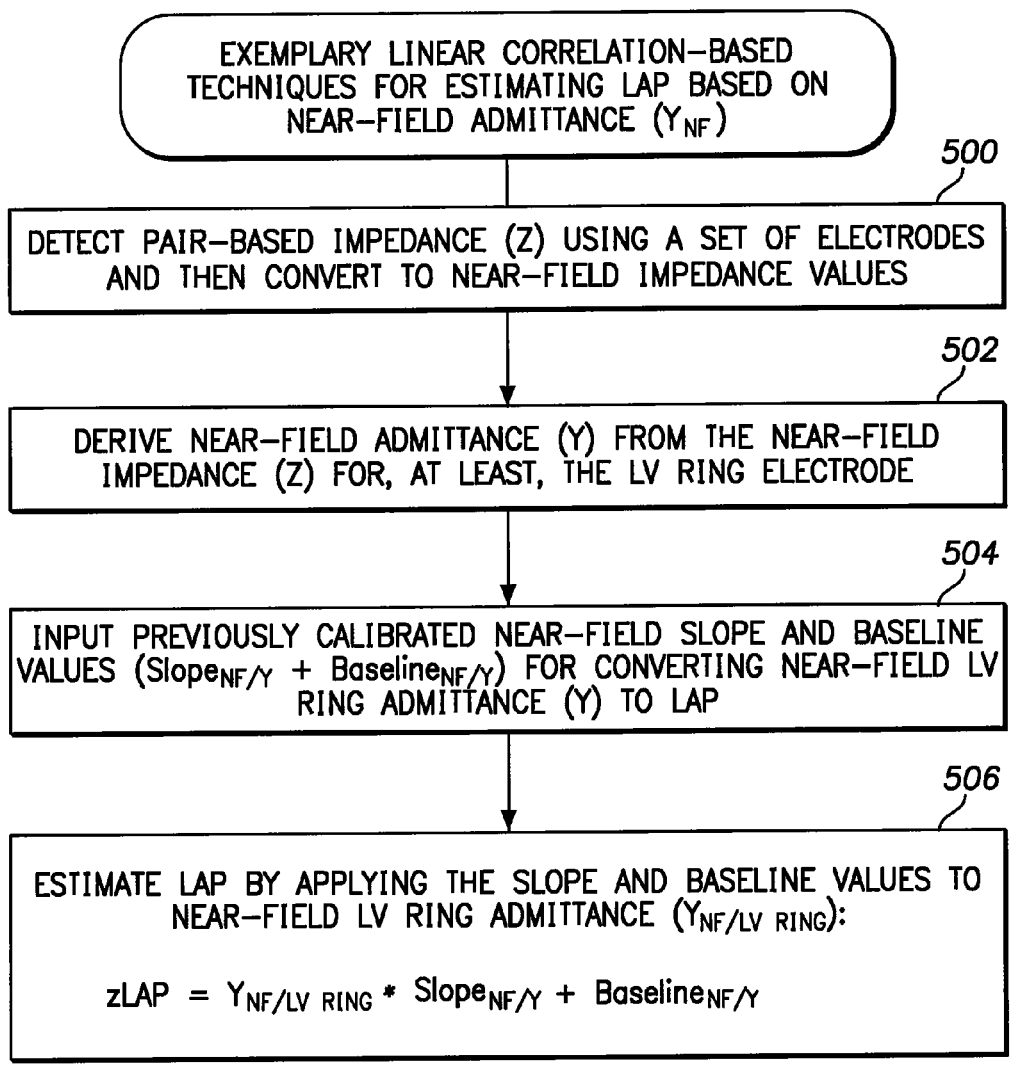
FIG. 19 summarizes an exemplary technique for use with the procedure of FIG. 11 to estimate LAP based on near-field admittance values derived from near-field impedance.

Turning now to FIG. 19, for the sake of completeness, a technique for calculating zLAP in response to near-field admittance values derived from signals initially detected based on vector-based impedance detection pulses will be described. This particular technique employs linear correlation using near-field admittance values but other correlation techniques can be used as well to calculate zLAP. At step 500, the pacer/ICD detects vector-based electrical impedance (Z) values along various sensing vectors and then converts the vector-based impedance values to near-field impedance values using the techniques discussed above. For example, the aforementioned six impedance vectors can be used to yield near-field impedance values for each of five individual electrodes.

At step 502, the pacer/ICD derives near-field admittance (Y) from the near-field electrical impedance values to obtain, at least, the near-field admittance for the LVring electrode. At step 505, the pacer/ICD inputs predetermined conversion factors from memory for converting near-field LVring admittance values to LAP. The conversion factors may be, e.g., predetermined slope and baseline values obtained during a calibration procedure employing linear regression and exploiting various physiologic maneuvers (e.g., Valsalva and Posture Maneuvers). Note that these near-field conversion factors will generally differ from vector-based conversion factors discussed in the prior applications (cited above) that were used to estimate LAP from vector-based impedance or admittance values.

At step 506, the pacer/ICD then estimates LAP within the patient by applying the conversion factors retrieved from memory (at step 505) to the near-field LVring admittance (obtained at step 502). When using slope and baseline conversion factors, LAP may be generally estimated by using:

$$zLAP = Y_{NF/LV\,RING} * Slope_{NF/Y} + Baseline_{NF/Y}$$

wherein the subscript NF is employed to designate that the relevant values are near-field values.

The formulae assume a linear relationship between LAP and the $Y_{NF/LV\,RING}$, which is an appropriate presumption, at least insofar as estimating LAP is concerned. Routine experimentation may be performed to determine whether a linear relationship is also suitable for use in estimating other particular cardiac pressure values, such as LV pressure, from near-field admittance values associated within other electrodes. Moreover, it should be understood that linear models need not necessarily be used, i.e. more sophisticated correlation models may instead by employed. Linear models are preferred in view of their simplicity.

As noted above, LAP is useful in detecting episodes of HF or cardiogenic PE. Reliable estimates of LAP also allow the dosing of heart failure medications (such as diuretics) to be properly titrated so as to minimize the number of episodes of acute heart failure decompensation. That is, accurate LAP monitoring provides for early identification of incipient HF decompensation and guides the adjustment of vasodilator and diuretic dosing.

Steps 500-506 may be repeated in a loop so as to update the estimated LAP. Estimates may be performed substantially in real-time so as to permit the pacer/ICD to continuously, or at least very frequently, calculate new LAP values. That is, in some implementations, a real-time LAP(t) function may be estimated based on near-field values so as to allow the pacer/ICD to track beat-to-beat changes in LAP. In particular, estimates of LAP based on near-field admittance may potentially be performed substantially in real-time based on near-field signals, assuming the pacer/ICD is appropriately configured. This allows the pacer/ICD to respond promptly to changes within the heart of the patient to detect conditions such as HF and cardiogenic PE. Appropriate therapy may then be delivered.

Note that the cardiac pressure value estimated using the techniques described herein is an effective intracardiac pressure ($P_{eff}$) not an absolute pressure. It represents the absolute intracardiac pressure less intrathoracic pressure:

$$P_{eff} = P_{intracardiac} - P_{intrathoracic}$$

That is, the effective pressure is a type of gauge pressure. Unless otherwise noted, all estimated cardiac pressure values discussed herein, particularly estimated LAP, are effective pressure values. In some examples described herein, the term "effective LAP" may be used as a reminder that effective pressures are used. In any case, effective pressure values are typically more useful from a clinical perspective than absolute pressure values.

In some implementations, different sets of conversion factors are stored within the pacer/ICD for use in converting the admittance values into LAP values depending on whether the patient is presently suffering an episode of acute mitral valve regurgitation (MR.) See, for example, the application cited above entitled "Systems and Methods for Estimating Left Atrial Pressure (LAP) in Patients with Acute Mitral Valve Regurgitation for use by an Implantable Medical Device." Still further, in some implementations, the device selectively suspends/cancels the LAP estimation procedure based on an assessment of the reliability of the LAP estimate made based on an analysis of various cardioelectric and cardiomechanical parameters. See U.S. patent application Ser. No. 12/109,304, filed Apr. 25, 2008, of Gutfinger et al., entitled "System and Method for Calibrating Cardiac Pressure Measurements Derived from Signals Detected by an Implantable Medical Device".

Thus, the use of near-field impedance facilitates estimates of LAP based on impedance/admittance. Note that, in implementations where therapy is automatically delivered in response to an elevated LAP or due to detecting of HF or cardiogenic PE, the pacer/ICD might be equipped to employ at least one other detection technique to corroborate the detection of the medical condition before therapy is delivered. Techniques for detecting or tracking heart failure are set forth the following patents and patent applications: U.S. Pat. No. 6,328,699 to Eigler et al., entitled "Permanently Implantable System and Method for Detecting, Diagnosing and Treating Congestive Heart Failure"; U.S. Pat. No. 6,970,742 to Mann et al., entitle "Method for Detecting, Diagnosing, and Treating Cardiovascular Disease"; U.S. Pat. No. 7,115,095 to Eigler et al., entitled "Systems and Methods for Detecting, Diagnosing and Treating Congestive Heart Failure"; U.S. patent application Ser. No. 11/100,008, of Kil et al., entitled "System and Method for Detecting Heart Failure and Pulmonary Edema based on Ventricular End-Diastolic Pressure using an Implantable Medical Device," filed Apr. 5, 2005; U.S. patent application Ser. No. 11/014,276, of Min et al., entitled "System and Method for Predicting Heart Failure based on Ventricular End-Diastolic Volume/Pressure using an Implantable Medical Device," filed Dec. 15, 2004; U.S. patent application Ser. No. 10/810,437, of Bornzin et al., entitled "System and Method for Evaluating Heart Failure Based on Ventricular End-Diastolic Volume Using an Implantable Medical Device," filed Mar. 26, 2004 and U.S. patent application Ser. No. 10/346,809, of Min et al., entitled "System and Method for Monitoring Cardiac Function via Cardiac Sounds Using an Implantable Cardiac Stimulation Device," filed Jan. 17, 2003. See also: U.S. Pat. No. 6,572,557, to Thou et al.; U.S. Pat. No. 6,645,153, to Kroll et al., entitled "System and Method for Evaluating Risk of Mortality Due To Congestive Heart Failure Using Physiologic Sensors," and U.S. Pat. No. 6,438,408 to Mulligan et al., entitled "Implantable Medical Device for Monitoring Congestive Heart Failure."

Although primarily described with respected to examples having a pacer/ICD, other implantable medical devices may be equipped to exploit the techniques described herein. For the sake of completeness, an exemplary pacer/ICD will now be described, which includes components for performing or controlling the various functions and steps already described.

Exemplary Pacer/ICD

Figure 21:
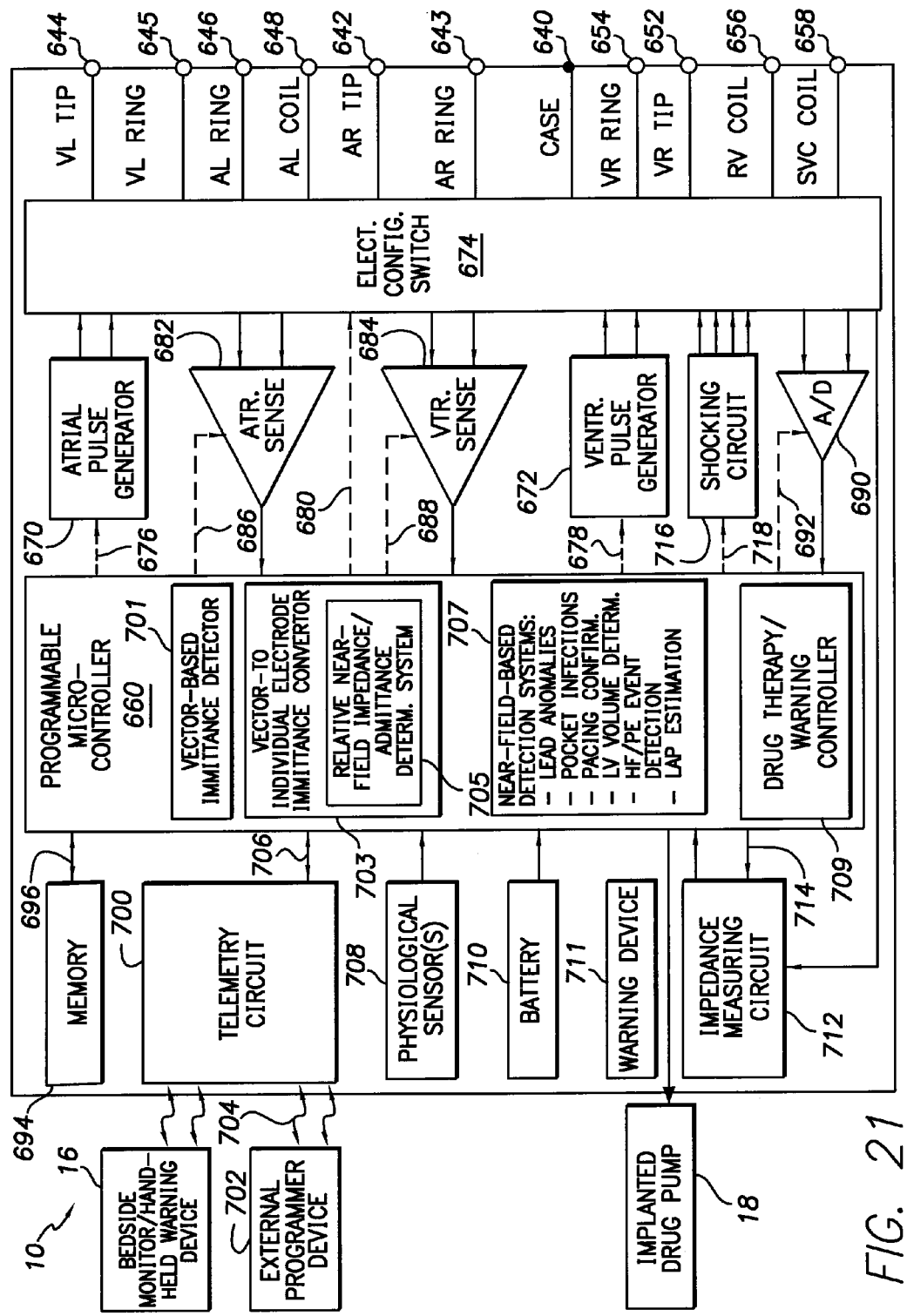
FIG. 21 is a functional block diagram of the pacer/ICD of FIG. 20, illustrating basic circuit elements that provide cardioversion, defibrillation and/or pacing stimulation in the heart and particularly illustrating components for performed the techniques of FIGS. 2-19.

With reference to FIGS. 20 and 21, a description of an exemplary pacer/ICD will now be provided. FIG. 20 provides a simplified block diagram of the pacer/ICD, which is a dual-chamber stimulation device capable of treating both fast and slow arrhythmias with stimulation therapy, including cardioversion, defibrillation, and pacing stimulation, and also capable of assessing near-field impedance or admittance. To provide other atrial chamber pacing stimulation and sensing, pacer/ICD 10 is shown in electrical communication with a heart 612 by way of a right atrial lead 620 having an atrial tip electrode 622 and an atrial ring electrode 623 implanted in the right atrial appendage. Pacer/ICD 10 is also in electrical communication with the heart by way of a right ventricular lead 630 having, in this embodiment, a ventricular tip electrode 632, a right ventricular ring electrode 634, a right ventricular (RV) coil electrode 636, and a superior vena cava (SVC) coil electrode 638. Typically, the right ventricular lead 630 is transvenously inserted into the heart so as to place the RV coil electrode 636 in the right ventricle, and the SVC coil electrode 638 in the superior vena cava. Accordingly, the right ventricular lead is capable of receiving cardiac signals, and delivering stimulation in the form of pacing and shock therapy to the right ventricle.

To sense left atrial and ventricular cardiac signals and to provide left chamber pacing therapy, pacer/ICD 10 is coupled to a CS lead 624 designed for placement in the "CS region" via the CS os for positioning a distal electrode adjacent to the left ventricle and/or additional electrode(s) adjacent to the left atrium. As used herein, the phrase "CS region" refers to the venous vasculature of the left ventricle, including any portion of the CS, great cardiac vein, left marginal vein, left posterior ventricular vein, middle cardiac vein, and/or small cardiac vein or any other cardiac vein accessible by the CS. Accordingly, an exemplary CS lead 624 is designed to receive atrial and ventricular cardiac signals and to deliver left ventricular pacing therapy using at least a left ventricular tip electrode 626 and a LV ring electrode 625, left atrial pacing therapy using at least a left atrial ring electrode 627, and shocking therapy using at least a left atrial coil electrode 628. With this configuration, biventricular pacing can be performed. Although only three leads are shown in FIG. 20, it should also be understood that additional leads (with one or more pacing, sensing and/or shocking electrodes) might be used and/or additional electrodes might be provided on the leads already shown.

A simplified block diagram of internal components of pacer/ICD 10 is shown in FIG. 21. While a particular pacer/ICD is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation. The housing 640 for pacer/ICD 10, shown schematically in FIG. 21, is often referred to as the "can", "case" or "case electrode" and may be programmably selected to act as the return electrode for all "unipolar" modes. The housing 640 may further be used as a return electrode alone or in combination with one or more of the coil electrodes, 628, 636 and 638, for shocking purposes. The housing 640 further includes a connector (not shown) having a plurality of terminals, 642, 643, 644, 645, 646, 648, 652, 654, 656 and 658 (shown schematically and, for convenience, the names of the electrodes to which they are connected are shown next to the terminals). As such, to achieve right atrial sensing and pacing, the connector includes at least a right atrial tip terminal ($A_R$ TIP) 642 adapted for connection to the atrial tip electrode 622 and a right atrial ring ($A_R$ RING) electrode 643 adapted for connection to right atrial ring electrode 623. To achieve left chamber sensing, pacing and shocking, the connector includes at least a left ventricular tip terminal ($V_L$ TIP) 644, a left ventricular ring terminal (V$_L$ RING) 645, a left atrial ring terminal (A$_L$ RING) 646, and a left atrial shocking terminal (A$_L$ COIL) 648, which are adapted for connection to the left ventricular tip electrode 626, left ventricular ring electrode 625, the left atrial ring electrode 627, and the left atrial coil electrode 628, respectively. To support right chamber sensing, pacing and shocking, the connector further includes a right ventricular tip terminal (V$_R$ TIP) 652, a right ventricular ring terminal (V$_R$ RING) 654, a right ventricular shocking terminal (V$_R$ COIL) 656, and an SVC shocking terminal (SVC COIL) 658, which are adapted for connection to the right ventricular tip electrode 632, right ventricular ring electrode 634, the V$_R$ coil electrode 636, and the SVC coil electrode 638, respectively.

At the core of pacer/ICD 10 is a programmable microcontroller 660, which controls the various modes of stimulation therapy. As is well known in the art, the microcontroller 660 (also referred to herein as a control unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 660 includes the ability to process or monitor input signals (data) as controlled by a program code stored in a designated block of memory. The details of the design and operation of the microcontroller 660 are not critical to the invention. Rather, any suitable microcontroller 660 may be used that carries out the functions described herein. The use of microprocessor-based control circuits for performing timing and data analysis functions are well known in the art.

As shown in FIG. 21, an atrial pulse generator 670 and a ventricular pulse generator 672 generate pacing stimulation pulses for delivery by the right atrial lead 620, the right ventricular lead 630, and/or the CS lead 624 via an electrode configuration switch 674. It is understood that in order to provide stimulation therapy in each of the four chambers of the heart, the atrial and ventricular pulse generators, 670 and 672, may include dedicated, independent pulse generators, multiplexed pulse generators or shared pulse generators. The pulse generators, 670 and 672, are controlled by the microcontroller 660 via appropriate control signals, 676 and 678, respectively, to trigger or inhibit the stimulation pulses.

The microcontroller 660 further includes timing control circuitry (not separately shown) used to control the timing of such stimulation pulses (e.g., pacing rate, AV delay, atrial interconduction (inter-atrial) delay, or ventricular interconduction (V-V) delay, etc.) as well as to keep track of the timing of refractory periods, blanking intervals, noise detection windows, evoked response windows, alert intervals, marker channel timing, etc., which is well known in the art. Switch 674 includes a plurality of switches for connecting the desired electrodes to the appropriate I/O circuits, thereby providing complete electrode programmability. Accordingly, the switch 674, in response to a control signal 680 from the microcontroller 660, determines the polarity of the stimulation pulses (e.g., unipolar, bipolar, combipolar, etc.) by selectively closing the appropriate combination of switches (not shown) as is known in the art.

Atrial sensing circuits 682 and ventricular sensing circuits 684 may also be selectively coupled to the right atrial lead 620, CS lead 624, and the right ventricular lead 630, through the switch 674 for detecting the presence of cardiac activity in each of the four chambers of the heart. Accordingly, the atrial (ATR. SENSE) and ventricular (VTR. SENSE) sensing circuits, 682 and 684, may include dedicated sense amplifiers, multiplexed amplifiers or shared amplifiers. The switch 674 determines the "sensing polarity" of the cardiac signal by selectively closing the appropriate switches, as is also known in the art. In this way, the clinician may program the sensing polarity independent of the stimulation polarity. Each sensing circuit, 682 and 684, preferably employs one or more low power, precision amplifiers with programmable gain and/or automatic gain control, bandpass filtering, and a threshold detection circuit, as known in the art, to selectively sense the cardiac signal of interest. The automatic gain control enables pacer/ICD 10 to deal effectively with the difficult problem of sensing the low amplitude signal characteristics of atrial or ventricular fibrillation. The outputs of the atrial and ventricular sensing circuits, 682 and 684, are connected to the microcontroller 660 which, in turn, are able to trigger or inhibit the atrial and ventricular pulse generators, 670 and 672, respectively, in a demand fashion in response to the absence or presence of cardiac activity in the appropriate chambers of the heart.

For arrhythmia detection, pacer/ICD 10 utilizes the atrial and ventricular sensing circuits, 682 and 684, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., AS, VS, and depolarization signals associated with fibrillation which are sometimes referred to as "F-waves" or "Fib-waves") are then classified by the microcontroller 660 by comparing them to a predefined rate zone limit (i.e., bradycardia, normal, atrial tachycardia, atrial fibrillation, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks).

Cardiac signals are also applied to the inputs of an analog-to-digital (A/D) data acquisition system 690. The data acquisition system 690 is configured to acquire intracardiac electrogram signals, convert the raw analog data into a digital signal, and store the digital signals for later processing and/or telemetric transmission to an external device 702. The data acquisition system 690 is coupled to the right atrial lead 620, the CS lead 624, and the right ventricular lead 630 through the switch 674 to sample cardiac signals across any pair of desired electrodes. The microcontroller 660 is further coupled to a memory 694 by a suitable data/address bus 696, wherein the programmable operating parameters used by the microcontroller 660 are stored and modified, as required, in order to customize the operation of pacer/ICD 10 to suit the needs of a particular patient. Such operating parameters define, for example, the amplitude or magnitude, pulse duration, electrode polarity, for both pacing pulses and impedance detection pulses as well as pacing rate, sensitivity, arrhythmia detection criteria, and the amplitude, waveshape and vector of each shocking pulse to be delivered to the patient's heart within each respective tier of therapy. Other pacing parameters include base rate, rest rate and circadian base rate.

Advantageously, the operating parameters of the implantable pacer/ICD 10 may be non-invasively programmed into the memory 694 through a telemetry circuit 700 in telemetric communication with the external device 702, such as a programmer, transtelephonic transceiver or a diagnostic system analyzer. The telemetry circuit 700 is activated by the microcontroller by a control signal 706. The telemetry circuit 700 advantageously allows intracardiac electrograms and status information relating to the operation of pacer/ICD 10 (as contained in the microcontroller 660 or memory 694) to be sent to the external device 702 through an established communication link 704. Pacer/ICD 10 further includes an accelerometer or other physiologic sensor (e.g., three-dimensional accelerometer capable of determining posture and activity) or sensors 708, sometimes referred to as a "rate-responsive" sensor because it is typically used to adjust pacing stimulation rate according to the exercise state of the patient.

However, physiological sensor(s) 708 can be equipped to sense any of a variety of cardiomechanical parameters, such as heart sounds, systemic pressure, etc. As can be appreciated, at least some these sensors may be mounted outside of the housing of the device and, in many cases, will be mounted to the leads of the device. Examples of physiological sensors that might be used with the device are described in: U.S. patent application Ser. No. 11/927,026, filed Oct. 29, 2007, of Nabutovsky et al., entitled "Systems and Methods for Exploiting Venous Blood Oxygen Saturation in combination with Hematocrit or Other Sensor Parameters for use with an Implantable Medical Device."

Moreover, the physiological sensor 708 may further be used to detect changes in cardiac output, changes in the physiological condition of the heart, or diurnal changes in activity (e.g., detecting sleep and wake states) and to detect arousal from sleep. Accordingly, the microcontroller 660 responds by adjusting the various pacing parameters (such as rate, AV delay, V-V delay, etc.) at which the atrial and ventricular pulse generators, 670 and 672, generate stimulation pulses. While shown as being included within pacer/ICD 10, it is to be understood that the physiologic sensor 708 may also be external to pacer/ICD 10, yet still be implanted within or carried by the patient. A common type of rate responsive sensor is an activity sensor incorporating an accelerometer or a piezoelectric crystal, which is mounted within the housing 640 of pacer/ICD 10. Other types of physiologic sensors are also known, for example, sensors that sense the oxygen content of blood, respiration rate and/or minute ventilation, pH of blood, ventricular gradient, etc., The pacer/ICD additionally includes a battery 710, which provides operating power to all of the circuits shown in FIG. 21. The battery 710 may vary depending on the capabilities of pacer/ICD 10. If the system only provides low voltage therapy, a lithium iodine or lithium copper fluoride cell typically may be utilized. For pacer/ICD 10, which employs shocking therapy, the battery 710 should be capable of operating at low current drains for long periods, and then be capable of providing high-current pulses (for capacitor charging) when the patient requires a shock pulse. The battery 710 should also have a predictable discharge characteristic so that elective replacement time can be detected. Accordingly, appropriate batteries are employed.

As further shown in FIG. 21, pacer/ICD 10 is shown as having an impedance measuring circuit 712, which is enabled by the microcontroller 660 via a control signal 714. Uses for an impedance measuring circuit include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring respiration; and detecting the opening of heart valves, etc. The impedance measuring circuit 712 is advantageously coupled to the switch 774 so that any desired electrode may be used. The impedance measuring circuit 712 also detects the impedance signals discussed above to use assessing near-field immittance. That is, impedance measuring circuit 712 is an electrical impedance (Z) detector operative to detect a vector-based electrical impedance (Z) signals within the patient along a plurality of sensing vectors from which near-field immittance values can be derived.

In the case where pacer/ICD 10 is intended to operate as an implantable cardioverter/defibrillator (ICD) device, it detects the occurrence of an arrhythmia, and automatically applies an appropriate electrical shock therapy to the heart aimed at terminating the detected arrhythmia. To this end, the microcontroller 660 further controls a shocking circuit 716 by way of a control signal 718. The shocking circuit 716 generates shocking pulses of low (up to 0.5 joules), moderate (0.5-10 joules) or high energy (11 to 40 joules or more), as controlled by the microcontroller 660. Such shocking pulses are applied to the heart of the patient through at least two shocking electrodes, and as shown in this embodiment, selected from the left atrial coil electrode 628, the RV coil electrode 636, and/or the SVC coil electrode 638. The housing 640 may act as an active electrode in combination with the RV electrode 636, or as part of a split electrical vector using the SVC coil electrode 638 or the left atrial coil electrode 628 (i.e., using the RV electrode as a common electrode). Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 7-40 joules), delivered asynchronously (since R-waves may be too disorganized), and pertaining exclusively to the treatment of fibrillation. Accordingly, the microcontroller 660 is capable of controlling the synchronous or asynchronous delivery of the shocking pulses.

Insofar as near-field-based systems are concerned, the microcontroller includes a vector-based immittance detector 701 operative to detect impedance, admittance or related immittance signals along vectors between a set of pairs of electrodes and vector-to-individual electrode immittance convertor 703 operative to convert the vector-based immittance measurements into individual electrode-based immittance values using techniques described above. To this end, convertor 703 includes a relative near-field impedance/admittance determination system 705 operative to determine values of relative near-field impedance, admittance (or related parameters) for individual electrodes. Additionally, the microcontroller includes a set of near-field immittance-based detection systems 707, including sub-systems directed to detecting lead anomalies, pocket infections, pacing confirmation, LV/RV volumes, HF/PE events, and LAP or other conditions or parameters, using techniques discussed above.

Diagnostic data pertaining to these or other conditions can be stored in memory 694. Warning and/or notification signals are generated, when appropriate, by a warning controller 709 then relayed to the bedside monitor 16 or to external programmer 702 (or other external system) via telemetry system 700. Alternatively, if an internal warning device 711 is provided, warnings may be generated using such a device for alerting the patient. Controller 709 is also equipped to control therapy, including controlling an implantable drug pump (if one is provided) to deliver appropriate medications. Terminals for connecting the implanted warning device and the implanted drug pump to the pacer/ICD are not separately shown.

Depending upon the implementation, the various components of the microcontroller may be implemented as separate software modules or the modules may be combined to permit a single module to perform multiple functions. In addition, although shown as being components of the microcontroller, some or all of these components may be implemented separately from the microcontroller, using application specific integrated circuits (ASICs) or the like.

At least some of the techniques described herein can be performed by (or under the control of) a suitably-equipped external device. For the sake of completeness, an exemplary device programmer will now be described, which includes components for performing or controlling at least some of the functions and steps already described.

Exemplary External Programmer

Figure 22:
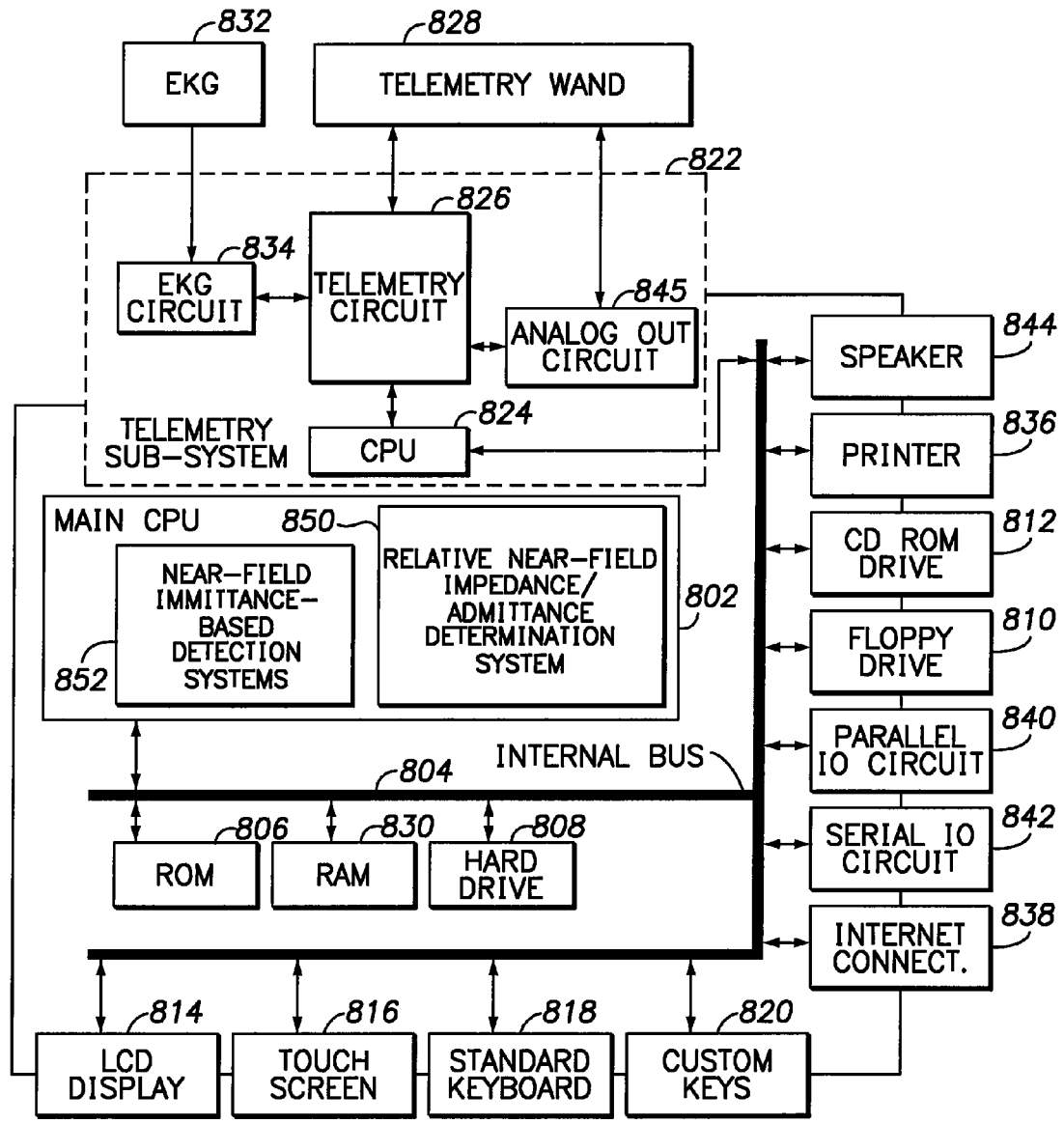
FIG. 22 is a functional block diagram illustrating components of a device programmer of FIG. 21, and in particular illustrating programmer-based components for performing or controlling the techniques of FIGS. 2-19.

FIG. 22 illustrates pertinent components of an external programmer 702 for use in programming the pacer/ICD of FIG. 21 and for performing the above-described calibration techniques. For the sake of completeness, other device programming functions are also described herein. Generally, the programmer permits a physician or other user to program the operation of the implanted device and to retrieve and display information received from the implanted device such as IEGM data and device diagnostic data. Additionally, the external programmer can be optionally equipped to receive and display electrocardiogram (EKG) data from separate external EKG leads that may be attached to the patient. Depending upon the specific programming of the external programmer, programmer 702 may also be capable of processing and analyzing data received from the implanted device and from the EKG leads to, for example, render preliminary diagnosis as to medical conditions of the patient or to the operations of the implanted device.

Now, considering the components of programmer 702, operations of the programmer are controlled by a CPU 802, which may be a generally programmable microprocessor or microcontroller or may be a dedicated processing device such as an application specific integrated circuit (ASIC) or the like. Software instructions to be performed by the CPU are accessed via an internal bus 804 from a read only memory (ROM) 806 and random access memory 830. Additional software may be accessed from a hard drive 808, floppy drive 810, and CD ROM drive 812, or other suitable permanent mass storage device. Depending upon the specific implementation, a basic input output system (BIOS) is retrieved from the ROM by CPU at power up. Based upon instructions provided in the BIOS, the CPU "boots up" the overall system in accordance with well-established computer processing techniques.

Once operating, the CPU displays a menu of programming options to the user via an LCD display 814 or other suitable computer display device. To this end, the CPU may, for example, display a menu of specific programmable parameters of the implanted device to be programmed or may display a menu of types of diagnostic data to be retrieved and displayed. In response thereto, the physician enters various commands via either a touch screen 816 overlaid on the LCD display or through a standard keyboard 818 supplemented by additional custom keys 820, such as an emergency VVI (EVVI) key. The EVVI key sets the implanted device to a safe VVI mode with high pacing outputs. This ensures life sustaining pacing operation in nearly all situations but by no means is it desirable to leave the implantable device in the EVVI mode at all times.

Once all pacing leads are mounted and the pacing device is implanted, the various parameters are programmed. Typically, the physician initially controls the programmer 702 to retrieve data stored within any implanted devices and to also retrieve EKG data from EKG leads, if any, coupled to the patient, along with any stored immittance data. To this end, CPU 802 transmits appropriate signals to a telemetry subsystem 822, which provides components for directly interfacing with the implanted devices, and the EKG leads. Telemetry subsystem 822 includes its own separate CPU 824 for coordinating the operations of the telemetry subsystem. Main CPU 802 of programmer communicates with telemetry subsystem CPU 824 via internal bus 804. Telemetry subsystem additionally includes a telemetry circuit 826 connected to telemetry wand 828, which, in turn, receives and transmits signals electromagnetically from a telemetry unit of the implanted device. The telemetry wand is placed over the chest of the patient near the implanted device to permit reliable transmission of data between the telemetry wand and the implanted device. Herein, the telemetry subsystem is shown as also including an EKG circuit 834 for receiving surface EKG signals from a surface EKG system 832. In other implementations, the EKG circuit is not regarded as a portion of the telemetry subsystem but is regarded as a separate component.

Typically, at the beginning of the programming session, the external programming device controls the implanted devices via appropriate signals generated by the telemetry wand to output all previously recorded patient and device diagnostic information. Patient diagnostic information includes, for example, recorded IEGM data and statistical patient data such as the percentage of paced versus sensed heartbeats. Device diagnostic data includes, for example, information representative of the operation of the implanted device such as lead impedances, battery voltages, battery recommended replacement time (RRT) information and the like, along with any recorded immittance signals. Data retrieved from the pacer/ICD also includes the data stored within the recalibration database of the pacer/ICD (assuming the pacer/ICD is equipped to store that data.) Data retrieved from the implanted devices is stored by external programmer 702 either within a random access memory (RAM) 830, hard drive 808 or within a floppy diskette placed within floppy drive 810. Additionally, or in the alternative, data may be permanently or semi-permanently stored within a compact disk (CD) or other digital media disk, if the overall system is configured with a drive for recording data onto digital media disks, such as a write once read many (WORM) drive.

Once all patient and device diagnostic data previously stored within the implanted devices is transferred to programmer 702, the implanted devices may be further controlled to transmit additional data in real time as it is detected by the implanted devices, such as additional IEGM data, lead impedance data, and the like. Additionally, or in the alternative, telemetry subsystem 822 receives EKG signals from EKG leads 832 via an EKG processing circuit 834. As with data retrieved from the implanted device itself, signals received from the EKG leads are stored within one or more of the storage devices of the external programmer. Typically, EKG leads output analog electrical signals representative of the EKG. Accordingly, EKG circuit 834 includes analog to digital conversion circuitry for converting the signals to digital data appropriate for further processing within the programmer. Depending upon the implementation, the EKG circuit may be configured to convert the analog signals into event record data for ease of processing along with the event record data retrieved from the implanted device. Typically, signals received from the EKG leads are received and processed in real time.

Thus, the programmer receives data both from the implanted devices and from optional external EKG leads. Data retrieved from the implanted devices includes parameters representative of the current programming state of the implanted devices. Under the control of the physician, the external programmer displays the current programmable parameters and permits the physician to reprogram the parameters. To this end, the physician enters appropriate commands via any of the aforementioned input devices and, under control of CPU 802, the programming commands are converted to specific programmable parameters for transmission to the implanted devices via telemetry wand 828 to thereby reprogram the implanted devices. Prior to reprogramming specific parameters, the physician may control the external programmer to display any or all of the data retrieved from the implanted devices or from the EKG leads, including displays of EKGs, IEGMs, and statistical patient information. Any or all of the information displayed by programmer may also be printed using a printer 836.

Additionally, CPU 802 can include a relative near-field impedance/admittance determination system 850 operative to input vector-based impedance, admittance or related signals detected by the implanted device (or other devices) along vectors between a set of pairs of electrodes implanted within a patient and further operative to convert the vector-based impedance measurements into individual electrode-based relative near-field impedance values using techniques describe above. Additionally, CPU 802 can include a set of near-field immittance-based detection systems 852, including sub-systems directed to detecting lead anomalies, pocket infections, pacing confirmation, LV volume, HF/PE events, and LAP or other conditions or parameters, using techniques discussed above, which may subsequently be displayed to the physician on a LCD display 814 or sent to a central server via an internet connection 838.

Programmer/monitor 702 also includes a modem or other internet connection 838 to permit direct transmission of data to other programmers via the public switched telephone network (PSTN) or other interconnection line, such as a T1 line or fiber optic cable. Depending upon the implementation, the modem may be connected directly to internal bus 804 may be connected to the internal bus via either a parallel port 840 or a serial port 842. Other peripheral devices may be connected to the external programmer via parallel port 840 or a serial port 842 as well. Although one of each is shown, a plurality of input output (IO) ports might be provided. A speaker 844 is included for providing audible tones to the user, such as a warning beep in the event improper input is provided by the physician. Telemetry subsystem 822 additionally includes an analog output circuit 845 for controlling the transmission of analog output signals, such as IEGM signals output to an EKG machine or chart recorder.

With the programmer configured as shown, a physician or other user operating the external programmer is capable of retrieving, processing and displaying a wide range of information received from the implanted devices and to reprogram the implanted device if needed. The descriptions provided herein with respect to FIG. 22 are intended merely to provide an overview of the operation of programmer and are not intended to describe in detail every feature of the hardware and software of the programmer and is not intended to provide an exhaustive list of the functions performed by the programmer.

Depending upon the implementation, the various components of the microcontroller may be implemented as separate software modules or the modules may be combined to permit a single module to perform multiple functions. In addition, although shown as being components of the microcontroller, some or all of these components may be implemented separately from the microcontroller, using ASICs or the like.

In general, while the invention has been described with reference to particular embodiments, modifications can be made thereto without departing from the spirit and scope of the invention. Note also that the term "including" as used herein is intended to be inclusive, i.e. "including but not limited to."

What is claimed is:

1. A method for use with an implantable medical device for implant within a patient, the method comprising:
    detecting vector-based immittance measurements within tissues of the patient using a plurality of electrodes coupled to the device;
    converting the vector-based immittance measurements to individual electrode-based immittance values, wherein the individual electrode-based immittance measurements corresponding to a particular electrode are relative near-field immittance values and the relative near-field immittance values are representative of the immittance of tissues in sufficiently close proximity to the electrode to exclude substantially all far-field immittance contributions;
    controlling at least one device function in response to the individual electrode-based immittance values; and
    detecting one or more cardiac parameters based on the relative near-field immittance values.

2. The method of claim 1 wherein converting the vector-based immittance measurements into relative near-field immittance values is achieved by ignoring far-field contributions to the vector-based impedance measurements.

3. The method of claim 2 wherein converting the vector-based immittance measurements into relative near-field immittance values includes:
    converting at least N vector-based impedance measurements (v1, v2, . . . , vN) into a set of linear equations to be solved while ignoring the far-field contributions to the impedance measurements, where N is at least three; and
    solving the set of linear equations to yield a set of relative near-field impedance values (e1, e2, . . . , eN).

4. The method of claim 3 further including converting the set of near-field impedance values (e1, e2, . . . , eN) into a corresponding set of near-field admittance values (a1, a2, . . . , aN).

5. The method of claim 4 further including estimating left atrial pressure (LAP) based on selected near-field admittance values (a1, a2, . . . , aN).

6. The method of claim 5 wherein the device is equipped with an LVring electrode and wherein the selected near-field admittance values are values corresponding to the LVring electrode.

7. The method of claim 6 wherein estimating LAP includes calculating left ventricular end diastolic volume (LV EDV) based on LVring admittance and then converting LV EDV into LAP.

8. The method of claim 7 wherein converting LV EDV into LAP is performed using an exponential formula.

9. The method of claim 6 wherein estimating LAP includes calculating:

$$zLAP = YNF/LV\ RING * SlopeNF/Y + BaselineNF/Y$$

where YNF/LV RING represents near-field admittance values associated with the LVring electrode and wherein SlopeNF/Y and BaselineNF/Y are predetermined values representative of a linear correlation of YNF/LV RING to patient LAP.

10. The method of claim 3 wherein the plurality of electrodes include: an LVring electrode, an RVring electrode, an RAring electrode, a case electrode and an RVcoil electrode.

11. The method of claim 10 wherein the vector-based impedance measurements include an LVring-case measurement, an RVring-case measurement, an RAring-case measurement, an RVcoil-case measurement, an LVring-RAring measurement, and an LVring-RVring measurement.

12. The method of claim 1 wherein detecting one or more cardiac parameters includes detecting changes in the relative near-field immittance corresponding to a selected electrode and associating that change with a change in fluid content and/or tissue composition within a corresponding anatomical structure associated with the electrode.

13. The method of claim 12 wherein the selected electrode is an LVring electrode and wherein the corresponding structure associated with the electrode includes one or more of a coronary vein, an LV chamber, an LV myocardium, and pericardial space of the heart of the patient.

14. The method of claim 12 wherein the selected electrode is an RVring electrode and wherein the corresponding structure associated with the electrode includes one or more of an RV chamber and RV myocardium of the heart of the patient.

15. The method of claim 12 wherein the selected electrode is an RAring electrode and wherein the corresponding structure associated with the electrode includes one or more of an RA chamber and RA myocardium of the heart of the patient.

16. The method of claim 12 wherein the selected electrode is a case electrode and wherein the corresponding structure associated with the electrode is a device pocket.

17. The method of claim 12 wherein the selected electrode is an RVcoil electrode and wherein the corresponding structure associated with the electrode includes one or more of an RV chamber and RV myocardium of the heart of the patient.

18. The method of claim 1 wherein the vector-based immittance measurements correspond to an impedance polygon.

19. The method of claim 18 wherein the vector-based immittance measurements correspond to an impedance triangle.

20. The method of claim 1 wherein detecting one or more cardiac parameters based on the relative near-field immittance values includes detecting parameters representative of changes in fluid volume content indicative of one or more of heart failure and pulmonary edema.

21. The method of claim 1 wherein detecting one or more cardiac parameters based on the relative near-field immittance values includes detecting parameters representative of lead anomalies including one or more of lead dislodgement, lead failure, lead infection, lead abrasion, and lead perforation of cardiac tissue.

22. The method of claim 1 wherein detecting one or more cardiac parameters based on the relative near-field immittance values includes detecting parameters representative of one or both of the onset of cardiac pacing and the termination of cardiac pacing.

23. The method of claim 1 wherein detecting one or more cardiac parameters based on the relative near-field immittance values includes estimating volumes which include one or more of left ventricular (LV) volume and pericardial fluid volume based on a near-field immittance signal corresponding to an LVring electrode.

24. The method of claim 1 wherein detecting one or more cardiac parameters based on the relative near-field immittance values includes estimating right ventricular (RV) volume based on a near-field immittance signal corresponding to an RVring electrode.

25. The method of claim 1 wherein detecting one or more cardiac parameters based on the relative near-field immittance values includes detecting parameters representative of lead pocket infection based on a near-field immittance signal corresponding to a device housing electrode.

26. The method of claim 1 wherein the vector-based immittance measurements are bipolar immittance measurements.

27. The method of claim 1 wherein the vector-based immittance measurements are quadripolar immittance measurements measured using a set of electrodes, wherein current electrodes of the set and corresponding voltage electrodes of the set are in close proximity to one another.

28. A system use with an implantable medical device for implant within a patient, the system comprising:
   a vector-based immittance detector operative to detect vector-based immittance measurements within tissues of the patient using a plurality of electrodes coupled to the device;
   a immittance converter operative to convert the vector-based immittance measurements into individual electrode-based immittance values, wherein the individual electrode-based immittance measurements corresponding to a particular electrode are relative near-field immittance values and the relative near-field immittance values are representative of the immittance of tissues in sufficiently close proximity to the electrode to exclude substantially all far-field immittance contributions; and
   a controller operative to control at least one device function in response to the individual electrode-based immittance values, wherein the at least one device function includes detecting one or more cardiac parameters based on the relative near-field immittance values.

29. A system use with an implantable medical device for implant within a patient, the system comprising:
   means for detecting vector-based immittance measurements within tissues of the patient using a plurality of electrodes coupled to the device;
   means for converting the vector-based immittance measurements into individual electrode-based immittance values, wherein the individual electrode-based immittance measurements corresponding to a particular electrode are relative near-field immittance values and the relative near-field immittance values are representative of the immittance of tissues in sufficiently close proximity to the electrode to exclude substantially all far-field immittance contributions; and
   means for controlling at least one device function in response to the individual electrode-based immittance values, wherein the at least one device function includes detecting one or more cardiac parameters based on the relative near-field immittance values.

* * * * *